United States Patent [19]

Bodor

[11] 4,160,099

[45] * Jul. 3, 1979

[54] LABILE, NON-HETEROCYCLIC QUATERNARY AMMONIUM SALT/ESTERS AS TRANSIENT DERIVATIVES

[75] Inventor: Nicolae S. Bodor, Lawrence, Kans.

[73] Assignee: Interx Research Corporation, Lawrence

[*] Notice: The portion of the term of this patent subsequent to Nov. 2, 1993, has been disclaimed.

[21] Appl. No.: 724,914

[22] Filed: Sep. 20, 1976

Related U.S. Application Data

[63] Continuation-in-part of Ser. No. 482,513, Jun. 24, 1974, Pat. No. 3,998,815.

[51] Int. Cl.$^2$ ............................................. C07C 93/18
[52] U.S. Cl. .............................. 560/110; 260/239 D; 260/326.43; 260/239 BC; 260/326.25; 260/239.3 D; 260/332.2 R; 544/141; 544/171; 544/174; 544/41; 544/92; 544/386; 544/351; 544/396; 546/85; 546/132; 546/133; 546/156; 546/238; 546/318; 548/336; 548/343; 548/341; 548/343; 560/253; 548/372; 542/427; 544/172
[58] Field of Search ................... 260/295 R, 295.5 R, 260/243 A, 477, 455 R; 560/253, 110

[56] References Cited

U.S. PATENT DOCUMENTS

| | | | |
|---|---|---|---|
| 3,396,127 | 8/1968 | Burness et al. | 260/268 R X |
| 3,576,813 | 4/1971 | Burness et al. | 260/295 R |
| 3,989,711 | 11/1976 | Bodor | 260/309 |
| 3,998,815 | 12/1976 | Bodor | 260/240 X |

OTHER PUBLICATIONS

French et al., J. Am. Chem. Soc., vol. 43, pp. 651 to 658 (1918).
Ulrich et al., J. Am. Chem. Soc., vol. 43, pp. 660 to 667 (1918).
Stewart et al., J. Am. Chem. Soc., vol. 55, pp. 4813 to 4819 (1933).
Eastman Kodak Co., Chemical Abstracts, vol. 70, abst. no. 37852a (1969), (abst. of French Pat. No. 1,503,463).

Primary Examiner—Alan L. Rotman
Attorney, Agent, or Firm—Bacon & Thomas

[57] ABSTRACT

Labile quaternary ammonium salts of the following formula (I) and (II) are provided:

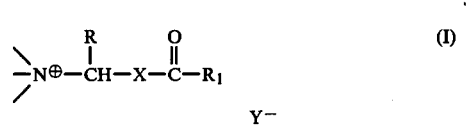

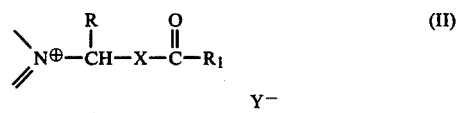

wherein

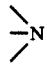

represents a tertiary aliphatic amine; wherein

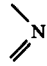

represents an unsaturated amine; wherein R represents a member selected from the group consisting of a hydrogen atom, a $C_1$–$C_8$ open chain or cyclo alkyl group, a $C_1$–$C_8$ alkoxyalkyl group, a $C_1$–$C_8$ acyloxyalkyl group, a $C_1$–$C_8$ haloalkyl group, a $C_1$–$C_8$ carboxyalkyl group, a $C_2$–$C_8$ alkenylphenyl group, an aryl group, and a substituted aryl group, whose substituents are selected from the group consisting of a halogen atom, an O-lower alkyl ($C_1$–$C_4$) group, an O-acyl group, a nitro group, a carboxyl group, and a carboethoxy group; wherein $R_1$ which may be the same or different, represents any member defined by R above with the proviso that $R_1$ cannot be a hydrogen atom; wherein X is —O— or —S—; and wherein Y represents a member selected from the group consisting of a halogen atom or any other organic or inorganic monovalent equivalent anion;

with the further proviso that

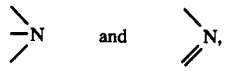

respectively cannot represent trimethylamine and pyridine or quinoline when R represents a hydrogen atom and $R_1$ represents a methyl group or a phenyl group.

The compounds described above are characterized by their extreme solubility and resistance to oxidation, dealkylation, and protonation prior to chemical and/or enzymatic hydrolysis. Upon chemical and/or enzymatic hydrolysis, these compounds will "cleave," thus releasing their active constituent or constituents, according to the following general scheme(s):

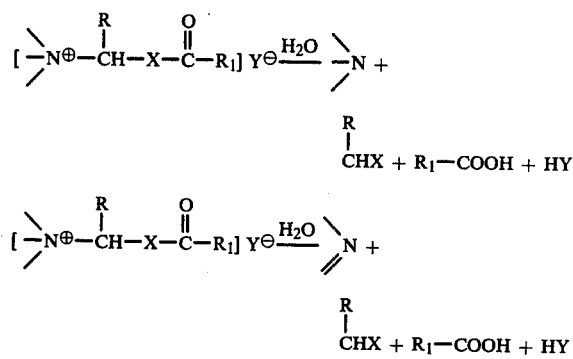

In other words, the title compounds hydrolyze (chemically or enzymatically) releasing a tertiary amine or unsaturated amine derivative, an aldehyde, a carboxylic acid and a hydrogen halide (HX) per the above reaction scheme.

7 Claims, 2 Drawing Figures

LABILE, NON-HETEROCYCLIC QUATERNARY AMMONIUM SALT/ESTERS AS TRANSIENT DERIVATIVES

CROSS-REFERENCE TO RELATED APPLICATIONS

This application is a continuation-in-part application of my earlier co-pending application, Ser. No. 482,513, now U.S. Pat. No. 3,998,815. A patent number has not yet been assigned to the parent application.

1. FIELD OF THE INVENTION

The present invention is directed to certain novel labile quaternary ammonium salts characterized as being transient. More particularly, the present invention extends to certain transient derivatives which could be characterized chemically as labile quaternary ammonium salts which exhibit extreme solubility and which protect its components (i.e., tertiary amine, aldehyde and carboxylic acid against oxidation, dealkylation and protonation, and yet, are predictably "cleaved" to release an active moiety and/or moieties.

For purposes of this application, the term "labile" denotes a quaternary ammonium salt of a tertiary (t) aliphatic amine or an unsaturated amine which is stable in the neat state, but when placed in an aqueous or alcoholic environment (preferentially slightly basic or acidic), or in biological systems (e.g., serum, blood, liver homogenate) will undergo enzymatic and/or acid or base cleavage, thus releasing the original tertiary aliphatic amine or unsaturated amine, or its proton salt.

The term "transient" pertains to a quaternary ammonium salt as described above, which, after chemical and/or enzymatic hydrolysis, will "cleave" into three (3) moieties (tertiary aliphatic amine or unsaturated amine, or a salt thereof, an aldehyde, and a carboxylic acid) in equal molecular amounts. That is, three transient derivatives are adequate for protecting and/or solubilizing tertiary aliphatic amines or unsaturated amines, aldehydes and carboxylic acids, prior to their chemical and/or enzymatic release for their intended use. Release occurs in such a manner that a sufficient amount of the compound intended to be delivered is available for its intended use.

For example, in the field of drug chemistry, and specifically, any conventional drug of known utility containing a tertiary aliphatic amine or unsaturated amine function as described in the above generic formula, such a drug is transformed into a remarkably more soluble labile quaternary ammonium salt, which after administration is resistant to extensive metabolism at or near the tertiary or unsaturated amine function, while the active tertiary or unsaturated amine is released following chemical and/or enzymatic hydrolysis at its therapeutic site of action. It is to this end that the present invention is primarily directed.

2. DESCRIPTION OF THE PRIOR ART

One of the basic methods of synthesis of the compounds encompassed within the above-described generic formula consists in reacting a compound of the formula (A) below, wherein R and $R_1$ are defined as above with a compound of the formula (B) below, wherein R, $R_1$,

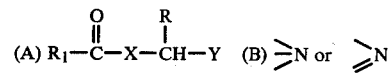

X and Y are defined as above:

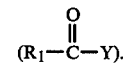

Some of the compounds of formula (A) above are old in the art and are formed by the reaction between an aldehyde (R—CHX) and an acyl halide

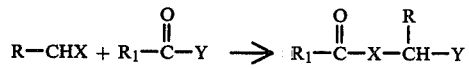

See, R. Adams and E. H. Vollweiler, *J. Amer. Chem. Soc.*, 40, 1732 (1918); H. E. French and R. Adams, ibid., 43, 651 (1921); L. H. Ulich and R. Adams, ibid., 43, 660 (1921).

Thus, preparation of the compounds of formula (A) can be described by reference to the following equation, wherein R and $R_1$ are defined as above:

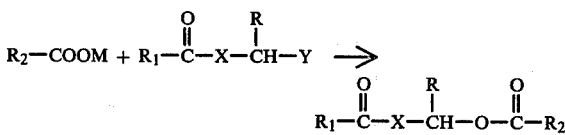

The compounds of formula (A) have been used in the past to protect a carboxy function in the following manner:

$$R_2\text{—COOM} + R_1\text{—}\overset{O}{\overset{\|}{C}}\text{—X—}\overset{R}{\overset{|}{CH}}\text{—Y} \longrightarrow$$

$$R_1\text{—}\overset{O}{\overset{\|}{C}}\text{—X—}\overset{R}{\overset{|}{CH}}\text{—O—}\overset{O}{\overset{\|}{C}}\text{—}R_2$$

In the above equation, R and $R_1$ are defined as above; $R_2$ represents the residue of ampicillin or a salicylic acid derivative; and M represents an alkali metal salt (Na, K, etc.). See, "Acyloxymethyl Esters of Ampicillin," W. V. Daehne, E. Fredriksen, E. Gundersen, F. Lund, P. Morch, H. J. Petersen, K. Roholt, L. Tybring, and W. V. Godfredsen, *J. Med. Chem.*, 13, 607 (1970), or British Pat. No. 1,220,457. While those compounds of formula (A) have been used as outlined above, i.e., protecting the carboxy function, this utility has no bearing on the invention disclosed and claimed herein. On the other hand, it is generally known that any activated haloalkyl compound (e.g., benzyl bromide or chloride) will react with a tertiary aliphatic amine to form the corresponding quaternary ammonium salt. However, this salt does not undergo hydrolytic cleavage, which is a necessary characteristic of the labile quaternary ammonium salts of this invention.

SUMMARY OF THE INVENTION

It is one object of the present invention to provide certain labile quaternary ammonium salts as transient derivatives, characterized by their extreme water solubility.

It is another object of the present invention to provide labile quaternary ammonium salts as described above which are protected against oxidation, dealkylation, and protonation prior to chemical and/or enzymatic hydrolysis.

Still, it is another object of the present invention to provide labile quaternary ammonium salts as described above which meet the above criteria and still are subject to chemical and/or enzymatic cleavage, thus releasing, on one hand, the original t-aliphatic amine or unsaturated amine, and on the other hand, an aldehyde and a carboxylic acid.

All of the foregoing objects are attained with the following compounds generically described in formulas (I) and (II) below:

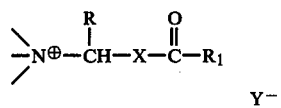 (I)

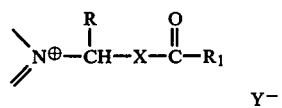 (II)

wherein

represents a tertiary aliphatic amine; wherein

represents an unsaturated amine; wherein R represents a member selected from the group consisting of a hydrogen atom, a $C_1$-$C_8$ open chain or cyclo alkyl group, a $C_1$-$C_8$ alkoxyalkyl group, a $C_1$-$C_8$ acyloxyalkyl group, a $C_1$-$C_8$ haloalkyl group, a $C_1$-$C_8$ carboxyalkyl group, a $C_2$-$C_8$ alkenylphenyl group, an aryl group, and a substituted aryl group, whose substituents are selected from the group consisting of a halogen atom, an O-lower alkyl ($C_1$-$C_4$) group, an O-acyl group, a nitro group, a carboxyl group, and a carboethoxy group; wherein $R_1$ which may be the same or different, represents any member defined by R above with the proviso that $R_1$ cannot be a hydrogen atom; wherein X is —O— or —S—; and wherein Y represents a member selected from the group consisting of a halogen atom or any other organic or inorganic monovalent equivalent anion;

with the further proviso that

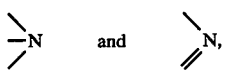

respectively cannot represent trimethylamine and pyridine or quinoline when R represents a hydrogen atom and $R_1$ represents a methyl group or a phenyl group.

In the above formulas, reference to "aryl" denotes a phenyl or naphthyl group; reference to "halo" and "halogen" in each occurrence denotes any suitable member of the halogen series, e.g., chlorine, bromine or iodine; and reference to "acyl" in the expression O-acyl denotes any convenient acyl group, such as a formyl group, an acetyl group, a propionyl group, a benzoyl group, etc. It is further noted that the term "substituted" insofar as substituted aryl is concerned refers to the fact that the aryl function may be substituted with any one or more of those substituents specifically defined herein. Finally, when constituent "X" is other than halogen, methanesulfonate, fluorosulfonate or tosylate are preferred.

As stressed earlier, the compounds of this invention are extremely useful where one wishes to protect a t-amine, unsaturated amine, aldehyde or carboxylic acid prior to their chemical and/or enzymatic release for their intended use.

DETAILED DESCRIPTION OF THE PREFERRED EMBODIMENTS

Figure 1:
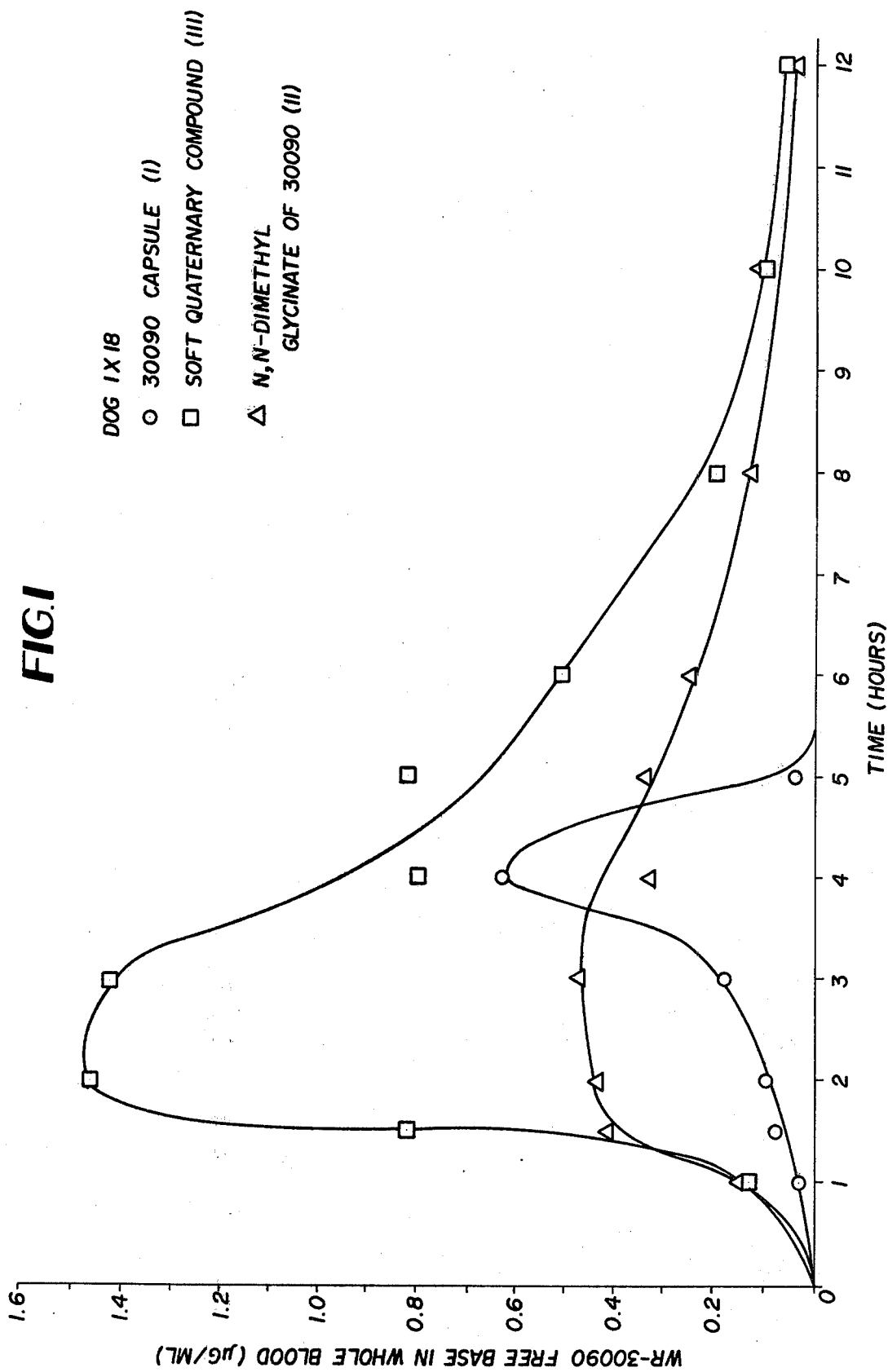

While all of the compounds encompassed within the above generic formula meet applicant's criteria, nevertheless, certain compounds remain preferred as set out below. A class of "most" preferred compounds is claimed hereinafter.

(1) 1-(Benzoyloxymethyl)-3-carbamoyl-pyridinium chloride
(2) 1-(α-Benzoyloxybenzyl)-3-carbamoyl-pyridinium bromide
(3) 1-(Cinnamoyloxymethyl)-3-carbamoyl-pyridinium chloride
(4) 1-(α-Benzoyloxyethyl)-3-carbamoyl-pyridinium chloride
(5) 1-(α-Cinnamoyloxyethyl)-3-carbamoyl-pyridinium chloride
(6) 1-(Benzoyloxymethyl)-ethylnicotinate chloride
(7) 1-(Cinnamoyloxymethyl)-ethylnicotinate chloride
(8) 1-(α-Benzoyloxybenzyl)-ethylnicotinate chloride
(9) 1-(α-Cinnamoyloxybenzyl)-ethylnicotinate chloride
(10) Benzoyloxymethyl-triethylammonium chloride
(11) α-Benzoyloxybenzyl-triethylammonium bromide
(12) Cinnamoyloxymethyl-triethylammonium chloride
(13) α-Benzoyloxyethyl-triethylammonium chloride
(14) α-Cinnamoyloxyethyl-triethylammonium chloride
(15) ω-(Diethyl-benzoyloxymethyl-ammonium)-2,6-dimethylacetanilide chloride
(16) ω-(Diethyl-α-benzoyloxybenzyl-ammonium)-2,6-dimethylacetanilide chloride
(17) ω-Diethyl-cinnamoyloxymethyl-ammonium)-2,6-dimethylacetanilide chloride
(18) ω-[Diethyl-(α-benzoyloxyethyl)-ammonium]-2,6-dimethylacetanilide chloride
(19) ω-[Diethyl-(α-cinnamoyloxyethyl)-ammonium]-2,6-dimethylacetanilide chloride
(20) N,N-dimethylglycine methyl ester-N-benzoyloxymethyl chloride
(21) N,N-diethylglycine ethyl ester-N-benzoyloxymethyl chloride
(22) ω-(Diethyl-pivaloyloxymethyl-ammonium)-2,6-dimethylacetanilide chloride
(23) N,N-dimethylglycine methyl ester-N-pivaloyloxymethyl chloride
(24) N,N-diethylglycine pyridine methanol ester-N-pivaloyloxymethyl chloride
(25) n-Octanoyloxymethylpyridinium chloride
(26) α-(n-Octanoyloxyethyl)pyridinium chloride
(27) 1-[α-Benzoyloxybenzyl]-3-methylimidazolium chloride
(28) 1-Benzoyloxymethyl-1,4-diazabicyclo[2.2.2]octane chloride

(29) 1-[α-Benzoyloxyethyl]-1,4-diazabicyclo[2.2.2]octane chloride
(30) 1-[α-Benzoyloxybenzyl]-1,4-diazabicyclo[2.2.2]octane chloride
(31) n-Butyryloxymethylquinuclidinium chloride
(32) α-Benzoyloxybenzylquinuclidinium chloride
(33) Benzoyloxymethylpilocarpine chloride
(34) n-Butyryloxyethyl-pilocarpine chloride
(35) [6,8-Dichloro-α-[dibutylaminomethyl]-2-[3',4'-dichlorophenyl]-4-quinolinemethyl-N]-benzoyloxymethyl-[N,N-dimethylglycinate chloride ]
(36) [6,8-Dichloro-α-[dibutylaminomethyl]-2-[3',4'-dichlorophenyl]-4-quinolinemethyl-N]-pivalyloxymethyl-[N,N-dimethylglycinate chloride]
(37) [6,8-Dichloro-α-[dibutylaminomethyl]-2-[3',4'-dichlorophenyl]-4-quinolinemethyl-N]-thioacetyloxymethyl-[N,N-dimethylglycinate chloride]
(38) [6,8-Dichloro-α-[dibutylaminomethyl]-2-[3',4'-dichlorophenyl]-4-quinolinemethyl-N]-[α-pivalyloxyethyl]-[N,N-dimethylglycinate chloride]
(39) [6,8-Dichloro-α-[dibutylaminomethyl]-2-[3',4'-dichlorophenyl]-4-quinolinemethyl-N]-[α-benzoyloxybenzyl]-[N,N-dimethylglycinate chloride]
(40) 3-[Dibutylamino]-1-[(2, b-bis-trifluoromethylphenyl)-4-pyridyl]propanol-N-benzoyloxymethyl-N,N-dimethylglycinate chloride
(41) 3-[Dibutylamino]-1-[2, b-bis-trifluoromethylphenyl)-4-pyridyl]propanol-N-pivalyloxymethyl-N,N-dimethylglycinate chloride
(42) 3-[Dibutylamino]-1-[2, b-bis-trifluoromethylphenyl)-4-pyridyl]propanol-N-thioacetyloxymethyl-N,N-dimethylglycinate chloride
(43) 3-[Dibutylamino]-1-[2, b-bis-trifluoromethylphenyl)-4-pyridyl]propanol-N-[α-benzoyloxybenzyl]-N,N-dimethylglycinate chloride
(44) Benzoyloxymethyldimethylbenzylammonium chloride
(45) [α-Benzoyloxybenzyl]dimethylbenzylammonium chloride
(46) 1-Thioacetyloxymethyl-3-methylimidazolium chloride
(47) N-Benzoyloxymethyl-tri-(2-n-propoxyethyl)-ammonium chloride
(48) N-Hexanoyloxymethyl-tri-(2-n-propoxyethyl)-ammonium chloride
(49) N-Acetyloxymethyl-tri-(2-n-propoxyethyl)-ammonium chloride
(50) N-Propionyloxymethyl-tri-(2-n-propoxyethyl)-ammonium chloride
(51) 1-(p-Chloro-α-phenylbenzyl)-4-methyl-4-benzoyloxymethylpiperazinium chloride
(52) 1-(p-Chloro-α-phenylbenzyl)-4-methyl-4-n-hexanoyloxymethylpiperazinium chloride
(53) 1-(p-Chloro-α-phenylbenzyl)-4-methyl-4-(α-benzoyloxyethylpiperazinium chloride
(54) 1-(p-Chloro-α-phenylbenzyl)-4-methyl-4-thioacetyloxymethylpiperazinium chloride
(55) N,N-Dimethyl-N-hexanoyloxymethyl-N'-phenyl-N'-(2-thenyl)-ethylene-diammonium chloride
(56) N,N-Dimethyl-N-benzoyloxymethyl-N'-phenyl-N'-(2-thenyl)-ethylene-diammonium chloride
(57) 10-[2-(1-Benzoyloxymethyl-1-pyrrolidinylium)ethyl]phenothiazine chloride
(58) 10-[2-(1-Thioacetyloxymethyl-1-pyrrolidinylium)ethyl]phenothiazine chloride
(59) β-Dimethylaminoethyl(p-chloro-α-methyl-benzhydryl)ether-N-benzoyloxymethyl chloride
(60) β-Dimethylaminoethyl(p-chloro-α-methyl-benzhydryl)ether-N-hexanoyloxymethyl chloride
(61) 4-Diphenylmethoxy-1-methyl-1-octanoyloxymethylpiperidinium chloride
(62) 4-Diphenylmethoxy-1-methyl-1-(p-toluyloxymethyl)piperidinium chloride
(63) 2,3,4,9-Tetrahydro-2-methyl-2-benzoyloxymethyl-9-phenyl-1H-indeno (2,1-c)pyridinium chloride
(64) 2,3,4,9-Tetrahydro-2-methyl-2-octanoyloxymethyl-9-phenyl-1H-indeno (2,1-c)pyridinium chloride
(65) 2,3,4,9-Tetrahydro-2-methyl-2-heptanoyloxymethyl-9-phenyl-1H-indeno (2,1-c)pyridinium chloride
(66) N-Ethylephedrine-benzoyloxymethyl chloride
(67) N-Ethylephedrine(α-benzoyloxyethyl) chloride
(68) N-Ethylephedrine-hexanoyloxymethyl chloride
(69) N-Ethylephedrine(α-acetyloxyethyl) chloride
(70) N-Ethylephedrine-thioacetyloxymethyl bromide
(71) 2-Diethylaminopropiophenone octanoyloxymethyl chloride
(72) 2-Diethylaminopropiophenone heptanoyloxymethyl chloride
(73) 2-Diethylaminopropiophenone(α-benzoyloxyethyl) chloride
(74) 2-Diethylaminopropiophenone-benzoyloxymethyl chloride
(75) 3,4-Dimethyl-2-phenyl-4-acetyloxymethyl-morpholinium chloride
(76) 3,4-Dimethyl-2-phenyl-4-benzoyloxymethyl-morpholinium chloride
(77) 3,4-Dimethyl-2-phenyl-4-pivalyloxymethyl-morpholinium chloride
(78) 6-Allyl-6,7-dihydro-5H-dibenz[c,e]-azepine-6-acetyloxymethyl bromide
(79) 6-Allyl-6,7-dihydro-5H-dibenz[c,e]-azepine-6-thioacetyloxymethyl chloride
(80) 6-Allyl-6,7-dihydro-5H-dibenz[c,e]-azepine-6-octanoyloxymethyl chloride
(81) Methyl 1,2,5,6-tetrahydro-1-methylnicotinate-1-benzoyloxymethyl chloride
(82) Methyl 1,2,5,6-tetrahydro-1-methylnicotinate-1-octanoyloxymethyl chloride
(83) methyl/ 1,2,5,6-tetrahydro-1-methylnicotinate-1-pivalyloxymethyl chloride
(84) Propionyl atropine N-acetyloxymethyl bromide
(85) Propionyl atropine N-hexanoyloxymethyl bromide
(86) (Bicyclohexyl)-1-carboxylic acid 2-(diethylamino)-ethyl ester N-hexanoyloxymethyl chloride
(87) (Bicyclohexyl)-1-carboxylic acid 2-(diethylamino)-ethyl ester N-acetyloxymethyl chloride
(88) (Bicyclohexyl)-1-carboxylic acid 2-(diethylamino)-ethyl ester N-pivalyloxymethyl chloride
(89) Diphenylthioacetic acid 5-(2-diethylaminoethyl)ester N-thioacetyl chloride
(90) Diphenylthioacetic acid 5-(2-diethylaminoethyl)ester N-hexanoyloxymethyl chloride
91) Diphenylthioacetic acid 5-(2-diethylaminoethyl)ester N-octanoyloxymethyl chloride
(92) 2-Butoxy-N-(2-N',N'-diethylaminoethyl)cinchoninamide N'-hexanoyloxymethyl chloride
(93) 2-Butoxy-N(2-N',N'-diethylaminoethyl)cinchoninamide N'-benzoyloxymethyl chloride
(94) 2-Butoxy-N-(2-N',N'-diethylaminoethyl)cinchoninamide N'-acetyloxymethyl chloride
(95) 2-Butoxy-N-(2-N',N'-diethylaminoethyl)cinchoninamide N'-thioacetyloxymethyl chloride
(96) 1-Methyl-2',6'-piperoloxylidide-1-pivalyloxymethyl chloride

(97) 1-Methyl-2',6'-piperoloxylidide-1-hexanoyloxymethyl chloride
(98) 1-Methyl-2',6'-piperoloxylidide-1-benzoyloxymethyl chloride
(99) 1-Pyrrolidineaceto-2',6'-xylidide-1-benzoyloxymethyl chloride
(100) 1-Pyrrolidineaceto-2',6'-xylidide-1-(α-benzoyloxyethyl)chloride
(101) 6-Dimethylamino-4,4-diphenyl-3-heptanone N-heptanoyloxymethyl chloride
(102) 6-Dimethylamino-4,4-diphenyl-3-heptanone N-acetyloxymethyl chloride
(103) 6-Dimethylamino-4,4-diphenyl-3-heptanone N-p-toluyloxymethyl chloride
(104) 6-Dimethylamino-4,4-diphenyl-3-heptanone N-(α-cinnamoyloxyethyl) chloride
(105) 4-Dimethylamino-3-methyl-1,2-diphenyl-2-butanol propionate N-benzoyloxymethyl chloride
(106) 4-Dimethylamino-3-methyl-1,2-diphenyl-2-butanol propionate N-hexanoyloxymethyl chloride
(107) 2-Chloro-10-[3-(N,N-dimethyl-N-acetyloxymethylammonium)phenothiazine chloride
(108) 2-Chloro-10-[3-(N,N-dimethyl-N-hexanoyloxymethylammonium)phenothiazine chloride
(109) Diazepam 4-acetyloxymethyl chloride
(110) Diazepam 4-trichloroacetyloxymethyl chloride
(111) Diazepam 4-thioacetyloxymethyl chloride
(112) Diazepam 4-(α-benzoyloxyethyl)bromide
(113) Nikethamide octanoyloxymethyl chloride
(114) Nikethamide cinnamoyloxymethyl chloride While the carbon chain length for the alkyl, alkoxyalkyl, acyloxyalkyl, haloalkyl, carboxyalkyl and alkenylphenyl moieties of the substituent "R" are limited to eight carbons, it is quite obvious from the specification as a whole that higher chain lengths are also operable.

The compounds of this invention can be conveniently prepared in the manner described below:

METHOD "A"

React an α-halo-ester of the general formula:

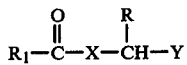

wherein R, R$_1$, X and Y are as defined as above, directly with a tertiary aliphatic amine

or an unsaturated amine

in approximately equimolecular proportions, in the presence of an inert solvent (ether, acetonitrile, CH$_2$Cl$_2$, etc.) at room temperature or at the reflux temperature of the solvent for 2-24 hours. As an alternative procedure, the above reaction can be carried out in the absence of a solvent by mixing the above two reactants together and maintaining them at room temperature or between 20°-70° C. for 2-24 hours. In both cases, the crystalline salt formed can be purified by crystallization from an ether-ethanol mixture, or the like.

METHOD "B"

The same compounds can be obtained by first mixing the tertiary aliphatic amine

or unsaturated amine

with an equimolecular amount of the corresponding acyl halide

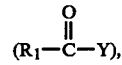

maintaining the mixture at room temperature for 2-24 hours. Then there is added to the reaction mixture an equimolecular amount of the aldehyde (R—CHO). The mixture is then stirred at room temperature or elevated temperature, up to 75° C., for 2-48 hours. Purification of the final product is carried out as in Method "A."

In the above description of Method "B," R, R$_1$, X and Y are defined as above.

A better understanding of the instant invention will be gained from a review of the following examples which are simply illustrative and not limitative of the present invention. Unless otherwise indicated, all temperature designations denote centigrade.

EXAMPLE 1

EXEMPLARY SOFT QUATERNIZING AGENTS (A) Chloromethyl benzoate: Chloromethyl benzoate was prepared using the method described by L. H. Ulich and R. Adams, J. Amer. Chem. Soc., 43, 660 (1921), bp 84°-85° (1.2 mm) [lit. bp 116° (10 mm)]; ir (neat) 3060, 2990, 1730, 1590, 1490, 1450, 1340, 1300, 1250, 1080, 800 and 720 cm$^{-1}$; pmr (CDCl$_3$) δ 7.0-8.2 (m, 5H) and 6.0 (s, 2H) ppm.

Following the procedure described for the preparation of the chloromethyl benzoate, the following chloroalkyl n-carboxylates were prepared:

(B) Chloromethyl n-octanoate: Chromatographed on florosil (petroleum ether 30°-60°); ir (neat) 2960, 2930, 1770, 1460, 1255, 1130, 1090, 1030 and 700 cm$^{-1}$; pmr (CDCl$_3$) δ 5.8 (s, 2H), 2.4 (t, 2H), 1.3 (bs, 10H) and 0.9 (bt, 3H) ppm.

Anal. Calcd for C$_9$H$_{17}$ClO$_2$: C, 56.10; H, 8.90. Found: C, 56.41; H, 9.01.

(C) Chloromethyl n-dodecanoate: Chromatographed on florosil (petroleum ether 30°-60°); ir (neat) 2960, 2930, 1770, 1465, 1260, 1100, 1030 and 710 cm$^{-1}$; pmr (CDCl$_3$) δ 5.8 (s, 2H), 2.4 (t, 2H), 1.3 (bs, 18H) and 1.0 (bt, 3H) ppm.

Anal. Calcd for C$_{13}$H$_{25}$ClO$_2$: C, 62.76; H, 10.13. Found: C, 63.07; H, 10.15.

(D) Chloromethyl n-tetradecanoate: Chromatographed on florosil (petroleum ether 30°-60°); ir (neat) 2960, 2920, 1770, 1460, 1255, 1100, 1030 and 700 cm$^{-1}$. pmr (CDCl$_3$) δ 5.8 (s, 2H), 2.4 (bt, 2), 1.3 (bs, 22H) and 0.9 (bt, 3H) ppm.

Anal. Calcd for $C_{15}H_{29}ClO_2$: C, 65.07; H, 10.56. Found. C, 65.40; H, 10.19.

(E) Chloromethyl n-hexadecanoate: mp 37°–39° (petroleum ether 30°–60°); ir (neat) 2960, 2920, 1770, 1460, 1255, 1100, 1030 and 700 cm⁻; pmr (CDCl$_3$) δ 5.8 (s, 2H), 2.4 (bt, 2H), 1.3 (bs, 26H) and 0.9 (bt, 3H) ppm.

Anal. Calcd for $C_{17}H_{33}ClO_2$: C, 66.97; H, 10.91. Found: C, 66.63; H, 10.55.

(F) α-Chloroethyl n-dodecanoate: Chromatographed on florosil (petroleum ether 30°–60°); ir (neat) 2950, 2920, 1750, 1450, 1370, 1270, 1140, 1080, 1020, 930 and 710 cm⁻¹; pmr (CDCl$_3$) δ 6.6 (q, 1H), 2.4 (t, 2H), 1.8 (d, 3H), 1.3 (bs, 18H) and 0.9 (bt, 3H) ppm.

Anal. Calcd for $C_{14}H_{27}ClO_2$: C, 63.98; H, 10.36. Found: C, 65.26; H, 10.55.

(G) α-Chloroethyl n-hexadecanoate: mp 35°–38° (petroleum ether 30°–60°); ir (neat) 2960, 2920, 1750, 1460, 1370, 1270, 1140, 1080, 940 and 670 cm⁻¹; pmr (CDCl$_3$) δ 6.6 (g, 1H), 2.4 (bt, 2H), 1.8 (d, 3H), 1.3 (bs, 26H) and 0.9 (bt, 3H) ppm.

Anal. Calcd for $C_{18}H_{35}ClO_2$: C, 67.79; H, 11.06. Found: C, 67.48; H, 11.15.

(H) Chloromethyl-thioacetate (1) Preparation of Hydroxymethylacetyl Sulfide 21.97 g (0.29 mole) thioacetic acid was deoxygenated with a N$_2$ stream for 15 min. Then 8.7 g (0.29 mol) paraformaldehyde was added and the mixture stirred and heated at 97° C. for 3 hrs. At this time all of the paraformaldehyde had gone into solution and the product was isolated by distillation. bp=60° C. (10 mm); yield—12.17 g (47% of theory); NMR δ 4.1 (HO-C, singlet) and δ 5.1 (S-CH$_2$-O, singlet).

(2) Preparation of Chloromethyl Thioacetate

To an ice-cooled solution of 24.3 g (0.12 mole) PCl$_5$ in 250 ml anhydrous ethyl ether, under N$_2$ and with stirring, was added 12.17 g (0.12 mole) hydroxymethylacetylsulfide, so slowly that the reaction temperature was never above 13° C. The reaction mixture was then allowed to warm to room temperature for 30 min. The ether was next evaporated and the residue set up for vacuum distillation of POCl$_3$ and the

POCl$_3$ distilled at 35° C. at 15 mm and the product distilled at 32° C. at 3 mm. Yield=4.81 g (34% of theory). NMR. δ 2.4 (H$_3$C=O, singlet); δ 4.95 (ClCH$_2$S, singlet).

EXAMPLE 2

α-BENZOYLOXYBENZYLPYRIDINIUM CHLORIDE

Benzoyl chloride 3.0 (0.021 mol) and 1.69 g (0.021 mol) pyridine were mixed together under nitrogen and allowed to react at room temperature overnite. Benzaldehyde 2.23 g (0.021 mol) was added and the mixture was allowed to stand at ambient temperature for 4 days. Recrystallization from ethanol:ether gave 4.27 g (0.013 mol), 62%, α-benzoyloxybenzylpyridinium chloride, mp 174.5°–176.5°.

Anal. Calcd for $C_{19}H_{16}ClNO_2$: C, 70.04; H, 4.95; N, 4.30. Found: C, 70.50; H, 5.50; N, 4.26.

EXAMPLE 3 n-OCTANOLOXYMETHYLPYRIDINIUM CHLORIDE (3)

a mixture of 1.93 g (0.01 mol) chloromethyl n-octanoate and 0.79 g (0.01 mol) pyridine were mixed and heated together at 90° for 3 hours. On cooling to room temperature, anhydrous ether was added to the mixture and the mixture was triturated in anhydrous ether overnight. The solid was isolated by filtration under a nitrogen atompshere and thoroughly washed with anhydrous ether. After drying in vacuo over calcium sulfate at room temperature, 1.90 g (0.007 mol), 70%, 3 was obtained as a white solid, mp 102°–107°, ir (KBr) 3430, 3040, 2970, 1770, 1635, 1490, 1110, 760, and 670 cm⁻¹; pmr (CDCl$_3$) δ 9.9 (d, 2H), 8.8 (t, 1H), 8.3 (t, 2H), 7.0 (s, 2H) 2.4 (t, 2H), 1.3 (bs, 10H) and 0.9 (bt, 3H) ppm.

Anal. Calcd for $C_{14}H_{22}ClNO_2.H_2O$: C, 58.02; H, 8.35; N, 4.83. Found: C, 57.51; H, 7.76; N, 4.58.

Using the procedure described for the preparation of 3, the following n-alkylcarboxymethylpyridinium salts were prepared:

EXAMPLE 4 n-DODECANOYLOXYMETHYLPYRIDINIUM CHLORIDE mp 120°–124°, ir (KBr) 3020, 2960, 1770, 1635, 1490, 1110, 760, and 670 cm⁻¹; pmr (CDCl$_3$) δ9.9 (d, 2H), 8.8 (t, 1H), 8.2 (t, 2H), 7.0 (s, 2H), 2.4 (t, 2H), 1.2 (bs, 19H) and 0.9 (bt, 3H) ppm.

Anal. Calcd for $C_{18}H_{30}ClNO_2$: C, 65.93; H, 9.22; N, 4.27. Found: C, 65.61; H, 9.42; N, 4.24.

EXAMPLE 5 n-TETRADECANOYLOXYMETHYL-PYRIDINIUM CHLORIDE mp 104°–109°; ir (KBr) 3420, 3010, 2960, 2920, 1770, 1638, 1485, 1470, 110, 760 and 670 cm⁻¹; pmr (CDCl$_3$) δ9.9 (d, 2H), 8.8 (t, 1H), 8.3 (t, 2H), 7.0 (s, 2H), 2.4 (t, 2H), 1.3 (bs, 22H) and 0.8 (bt, 3H) ppm.

Anal. Calcd for $C_{20}H_{34}ClNO_2.H_2O$: C, 64.23; H, 9.70; N, 3.75. Found: c, 63.55; H, 9.25; N, 3.60.

EXAMPLE 6 n-HEXADECANOYLOXYMETHYL-PYRIDINIUM CHLORIDE mp 132°–135°; ir (KBr) 3430, 3020, 29070, 2930, 1770, 1635, 1490, 1470, 1110, 760 and 670 cm⁻¹; pmr (CDCl$_3$) δ9.9 (d, 2H), 8.8 (t, 1H), 8.3 (t, 2H), 7.0 (s, 2H), 2.4 (t, 2H), 1.3 (bs, 26H) and 0.9 (bt, 3H) ppm.

Anal. Calcd for $C_{22}H_{38}ClNO_2$: C, 68.81; H, 9.97; N, 3.65. Found: C, 68.59; H, 9.97; N, 3.60.

EXAMPLE 7

1-BENZOYLOXYMETHYL-3-CARBOETHOX-YPYRIDINIUM CHLORIDE

A mixture of 3.00 g (0.02 mol) ethyl nicotinate and 3.50 g (0.02 mol) chloromethyl benzoate was heated at 70° under nitrogen for 10 hrs. Trituration in anhydrous ether and recrystallization from ethanol-ether gave 2.18 g (0.007 mol), 35%, 1-benzoyloxymethyl-3-carboethoxypyridinium chloride, mp 138°–141°; ir (KBr) 1730 cm⁻¹; pmr (CDCl$_3$) δ 1.43 (t, 3H), 4.47 (q, 2H), 7.7–7.3 (m, 5H), 8.2–7.95 (m, 2H), 9.17–8.50 (m, 4), 10.0 (bs, 1H) and 10.2 (bd, 1H) ppm.

Anal. Calcd for $C_{16}H_{16}ClNO_4$: C, 60.47; H, 5.08; N, 4.41. Found: C, 60.02; H, 5.05; N, 4.41.

EXAMPLE 8

1-n-DODECANOYLOXYMETHYL-N-ETHYLINICOTINAMIDE CHLORIDE (8)

2.49 g (0.01 mol) chloromethyl n-dodecanoate and 1.50 g (0.01 mol) N-ethyl nicotinamide were mixed and heated together at 90° for 1 hour. On cooling to room temperature, anhydrous ether was added to the mixture and the mixture was triturated in anhydrous ether overnite. The solid was isolated by filtration under a nitrogen atmosphere and thoroughly washed with anhydrous ether. After drying in vacuo over calcium sulfate at room temperature, 2.6 g (0.007 mol), 70%, 8 was obtained as a white solid mp 131°–135°; ir (KBr) 3220, 3060, 2965, 2930, 1770, 1680, 1640, 1470, 1110 and 670 cm$^{-1}$; pmr (CDCl$_3$) δ 10.5 (s, 1H), 9.8 (m, 3H), 8.3 (t, 1H), 6.8 (s, 2H), 3.6 (q, 2H), 2.5 (t, 2H), 1.3 (bs, 21H) and 0.9 (bt, 3H) ppm.

Anal. Calcd for $C_{21}H_{35}ClN_2O_3$: C, 63.22; H, 8.84; N, 7.02. Found: C, 62.70; H, 8.63; N, 6.90.

EXAMPLE 9

1-[α-BENZOYLOXYBENZYL]-3-METHYLIMIDAZOLIUM CHLORIDE (9)

To an ether solution of benzoyl chloride 2.81 g (0.02 mol) there was added dropwise 1.67 g (0.02 mol) 1-methylimidazole with stirring. The resulting mixture was evaporated in vacuo and the residue was allowed to react with 2.12 g (0.02 mol) benzaldehyde at 70° overnite. After cooling, the reaction mixture was triturated with ether and the solid separated by filtration. Recrystallization from dichloromethane:dioxane gave 4.2 g (0.012 mol), 65%, 9, mp 199°–201°; ir (KBr) 1740 cm$^{-1}$; pmr (CDCl$_3$) δ 4.17 (s, 3H), 8.18–7.25 (m, 12H), 8.50 (s, 1H) and 11.1 (bs, 1H) ppm.

Anal. Calcd for $C_{18}H_{17}ClN_2O_2$: C, 65.75; H, 5.21; N, 8.52. Found: C, 65.49; H, 5.22; N, 8.68.

EXAMPLE 10

1-n-DODECANOYLOXYMETHYL-3-METHYLIMIDAZOLIUM CHLORIDE (10)

A mixture of 2.49 g (0.01 mol) chloromethyl n-dodecanoate and 0.82 g (0.01 mol) 1-methylimidazole were mixed and heated together at 90° for 3 hrs. On cooling to room temperature, anhydrous ether overnite. The solid was isolated by filtration under a nitrogen atmosphere and thoroughly washed with anhydrous ether. After drying in vacuo over calcium sulfate at room temperature, 2.4 g (0.007 mol), 70%, 10 was obtained as a white solid, mp 60°–63°; ir (KBr) 3400, 3110, 2960, 2920, 1750, 1470, 1140 and 770 cm$^{-1}$; pmr (CDCl$_3$) δ 10.8 (s, 1H), 8.0 (d, 2H), 6.4 (s, 2H), 4.2 (s, 3H), 2.4 (t, 2H), 1.4 (bs, 18H) and 0.9 (bt, 3H) ppm.

Anal. Calcd for $C_{16}H_{31}ClN_2O_2.H_2O$: C, 58.52; H, 9.53; N, 8.03. Found: C, 58.85; H, 9.54; N, 8.79.

Using the procedure described for the preparation given in Example 10 the following n-alkylcarboxymethyl-3-methylimidazolium salts were prepared.

EXAMPLE 11

1-n-TETRADECANOYLOXYMETHYL-3-METHYLIMIDAXOLIUM CHLORIDE mp 68°–74°; ir (KBr) 3400, 3180, 2960, 2920, 1750, 1470, 1140 and 770 cm$^{-1}$; pmr (CDCl$_3$) δ 10.8 (s, 1H), 8.0 (d, 2H), 6.4 (s, 2H), 4.2 (s, 3H), 2.4 (t, 2H), 1.2 (bs, 22H) and 0.9 (bt, 3H) ppm.

Anal. Calcd for $C_{19}H_{35}ClN_2O_2.H_2O$: C, 57.77; H, 9.95; N, 7.38. Found: C, 58.85; H, 9.59; N, 7.38.

EXAMPLE 12

1-n-HEXADECANOYLOXYMETHYL-3-METHYLIMIDAZOLIUM CHLORIDE mp 80°–84°; ir (KBr) 3410, 3110, 2960, 2925, 1760, 1470, 1140 and 750 cm$^{-1}$; pmr (CDCl$_3$) δ 10.8 (s, 1H), 8.0 (d, 2H), 6.4 (s, 2H), 4.2 (s, 3H), 2.4 (t, 2H), 1.3 (bs, 26H) and 0.9 (bt, 3H) ppm.

Anal. Calcd for $C_{21}H_{39}ClN_2O_2.H_2O$: C, 62.27; H, 10.20; N, 6.92. Found: C, 62.13; H, 10.40; N, 7.41.

EXAMPLE 13

1-]α-n-DODECANOYLOXYETHYL]-3-METHYLIMIDAZOLIUM CHLORIDE mp 54°–59°; ir (KBr) 3440, 3060, 2920, 2840, 1740, 1500, 1465, 1150, 1050 and 750 cm$^{-1}$; pmr (CDCl$_3$) δ 10.7 (s, 1H), 8.0 (s, 1H), 7.7 (s, 1H), 7.1 (q, 1H), 4.2 (s, 3H), 2.4 (m, 2H), 2.0 (d, 3H), 1.3 (bs, 18H) and 0.9 (bt, 3H) ppm.

Anal. Calcd for $C_{18}H_{33}ClN_2O_2.H_2O$: C, 59.56; H, 9.72; N, 7.72. Found: C, 59.13; H, 9.88; N, 7.39.

EXAMPLE 14

1-[α-n-HEXADECANOYLOXYETHYL]-3-METHYLIMIDAZOLIUM CHLORIDE mp 68°–71°; ir (KBr) 3440, 3020, 2920, 2840, 1740, 1580, 1470, 1180, 1150, 1100, 1050, 940 and 750 cm$^{-1}$; pmr (CDCl$_3$) δ 10.8 (s, 1H), 8.0 (s, 1H), 7.7 (s, 1H), 7.1 (q, 1H), 4.2 (s, 3H), 2.3 (m, 2H), 1.9 (d, 3H), 1.2 (bs, 26H) and 0.9 (bt, 3H) ppm.

Anal. Calcd for $C_{22}H_{41}ClN_2O_2.H_2O$: C, 63.05; H, 10.34; N, 6.69. Found: C, 63.00; H, 10.61; N, 6.74.

EXAMPLE 15

1-BENZOYLOXYMETHYL-1,4-DIAZABICYCLO [2.2.2] OCTANE CHLORIDE

A mixture containing 2.24 g (0.02 mol) 1,4-diazabicyclo [2.2.2] Octane and 3.50 g (0.02 mol) chloromethyl benzoate was allowed to react at ambient temperature for 48 hr. Trituration in anhydrous ether and recrystallization from ethanol:ether gave 4.32 g (0.016 mol), 80% 1-benzoyloxymethyl-1,4-diazabicyclo [2.2.2] octane chloride, mp 208°–209° (dec), pmr (D$_2$O) δ 3.50 (q, 12H), 7.5–7.9 (m, 3H) and 8.1–8.3 (m, 2H) ppm.

Anal. Calcd for $C_{14}H_{19}ClNO_2$: C, 59.46; H, 6.79; N, 9.91. Found: C, 59.03; H, 6.80; N, 9.73.

EXAMPLE 16

1-n-DODECANOYLOXYMETHYL-1,4-DIAZABICYCLO [2.2.2] OCTANE CHLORIDE (16)

2.49 g (0.01 mol) chloromethyl n-dodecanoate and 1.12 g (0.01 mol) 1,4-diazabicyclo [2.2.2] octane were mixed and allowed to react together at room temperature for 72 hours. Anhydrous ether was added to the mixture and the mixture was triturated in anhydrous ether overnite. The solid was isolated by filtration under a nitrogen atmosphere and thoroughly washed with anhydrous ether. After drying in vacuo over calcium sulfate at room temperature, 2.0 g (0.006 mol), 60%, 16 was obtained as a white solid, mp 106°–110°, ir (KBr) 3400, 2960, 2920, 1760, 1460, 1120, 1080, 1050, 850 and 830 cm$^{-1}$; pmr (CDCl$_3$) δ 5.8 (s, 2H), 4.2–3.0 (mq, 12H), 2.6 (t, 2H), 1.3 (bs, 18H), and 0.9 (bt, 3H) ppm.

Anal. Calcd for C$_{19}$H$_{37}$ClN$_2$O$_2$·H$_2$O: C, 60.21; H, 10.37; N, 7.39. Found: C, 60.86; H, 10.12; N, 7.68.

EXAMPLE 17 n-DODECANOYLOXYMETHYLQUINUCLIDINIUM CHLORIDE (17)

2.49 g (0.01 mol) chloromethyl n-dodecanoate and 1.12 g (0.01 mol) quinuclidine were mixed and allowed to react together at room temperature for 48 hrs. Anhydrous ether was added to the mixture and the mixture was triturated in anhydrous ether overnite. The solid was isolated by filtration under a nitrogen atmosphere and thoroughly washed with anhydrous ether. After drying in vacuo over calcium sulfate at room temperature, 2.1 g (0.006 mol), 17 was obtained as a white solid, mp 170°–172°; ir (KBr) 2960, 2930, 1765, 1470, 1120, 1090, 860 and 830 cm$^{-1}$; pmr (CDCl$_3$) δ 5.8 (s, 2H), 3.9 (t, 6H), 2.5 (t, 2H), 2.2 (m, 7H), 1.3 (bs, 18H) and 0.9 (t, 3H) ppm.

Anal. Calcd for C$_{20}$H$_{38}$ClNO$_2$: C, 66.73; H, 10.64; N, 3.89. Found: C, 65.92; H, 10.58; N, 3.79.

EXAMPLE 18

ω-DIETHYLBENZOYLOXYMETHYLAMMONIUM-2,6-DIMETHYLACETANILIDE CHLORIDE

A mixture of 4.68 g (0.02 mol) ω-diethylamino-2,6-dimethylacetanilide (lidocaine) and 3.50 g (0.02 mole) chloromethyl benzoate was heated at 70° under nitrogen for 24 hr. Trituration in anhydrous ether and recrystallization from ethanol:ether gave 7.0 g (0.017 mol), 85%, ω-diethylbenzoyloxymethylammonium-2,6-dimethylacetanilide chloride, mp 153°–153.5°, pmr (CDCl$_3$) δ 1.60 (t, 6H), 2.33 (s, 6H, 3.82 (q, 4H), 5.22 (s, 2H), 6.08 (s, 2H), 7.05 (s, 3H), 7.5–7.8 (m, 3H), 8.1–8.3 (m, 2H) and 11.25 (s, 1H) ppm.

Anal. Calcd for C$_{22}$H$_{29}$ClNO$_3$: C, 65.25; H, 7.23; N, 6.92. Found: C, 65.53; H, 7.50; N, 6.84.

EXAMPLE 19

ω-DIETHYLPIVALOYLOXYMETHYLAMMONIUM-2,6-DIMETHYLACETANILIDE CHLORIDE

A mixture of 5.0 g (0.02 mol) ω-diethylamino-2,6-dimethylacetanilide (lidocaine) and 3.31 g (0.02 mol) chloromethyl pivalate was heated at 50° for 48 hr. Trituration in anhydrous ether and recrystallization from ethanol:ether gave 6.17 g (0.016 mol), 80%, ω-diethylpivaloyloxymethylammonium-2,6-dimethylacetanilide chloride, mp 162.5°–164°, pmr (CDCl$_3$) δ 1.3 (s, 9H), 1.5 (t, 6H), 2.2 (s, 6H), 3.7 (q, 4H), 5.0 (s, 2H), 5.7 (s, 2H), 7.0 (s, 3H) and 11.0 (s, 1H) ppm.

Anal. Calcd for C$_{20}$H$_{33}$ClN$_2$O$_3$: C, 62.40; H, 8.64; N, 7.28. Found: C, 62.09; H 8.86; N, 7.10.

EXAMPLE 20

PIVALOYLOXYMETHYLPILOCARPINE CHLORIDE

A mixture of 1.05 g (0.005 mol) pilocarpine and 0.75 g (0.005 mol) chloromethyl pivalate were mixed and heated together at 70° for 50 hr. Recrystallization from ethanol:ether gave 1.49 g (0.004 mol), 80%, pivaloyloxymethylpilocarpine chloride, mp 166° (dec), uv (CHCl$_3$) γ219 nm, ε=4835 M$^{-1}$ cm$^{-1}$; [α]$^{29°}$$_D$ = +57.4° (c=5, ethanol).

Anal. Calcd for C$_{17}$H$_{27}$ClN$_2$O$_4$: C, 56.89; H, 7.58; N, 7.81. Found: C, 56.25; H, 7.68; N, 7.68.

EXAMPLE 21 n-DODECANOYLOXYMETHYLPILOCARPINE CHLORIDE (21)

A mixture of 2.48 g (0.01 mol) chloromethyl n-dodecanoate and 2.08 g (0.01 mol) pilocarpine were mixed and heated together at 90° for 3 hours. On cooling to room temperature, anhydrous ether was added to the mixture and the mixture was triturated in anhydrous ether overnight. The solid was isolated by filtration under a nitrogen atmosphere and thoroughly washed with anhydrous ether. After drying in vacuo over calcium sulfate at room temperature, 3.19 g (0.007 mol), 70%, 21 was obtained as a white, hygroscopic solid, mp 58°–61°, pmr (CDCl$_3$) δ 10.3 (s, 1H), 7.7 (s, 1H), 6.3 (s, 2H), 4.6–3.6 (7H), 3.4–1.5 (7H), 1.3 (bs, 20H) and 0.9 (bt, 3H) ppm.

Anal. Calcd for C$_{24}$H$_{41}$ClN$_2$O$_4$: C, 63.07; H, 9.04; N, 6.13. Found: C, 63.11; H, 9.18; N, 6.34.

Following the procedure described in Example 21, the following n-alkylcarboxyalkylpilocarpine quaternary salts were prepared:

EXAMPLE 22 n-TETRADECANOYLOXYMETHYLPILOCARPINE CHLORIDE mp 59°–64°; pmr (CDCl$_3$) δ 10.4 (s, 1H), 7.8 (s, 1H), 6.3 (s, 2H), 4.5–3.7 (7H), 3.3–1.5 (7H), 1.2 (bs, 24H) and 0.9 (bt, 3H) ppm.

Anal. Calcd for C$_{26}$H$_{45}$ClN$_2$O$_4$: C, 64.37; H, 9.35; N, 5.78. Found: C, 64.14; H, 9.31; N, 5.98.

EXAMPLE 23 n-HEXADECANOYLOXYMETHYLPILOCARPINE CHLORIDE mp 67°–72°; ir (KBr) 3020, 2900, 2840, 1740, 1550, 1450, 1370, 1160, 1120, 1015 and 965 cm$^{-1}$; uv (CHCl$_3$) λ239 nm, ε=917 M$^{-1}$ cm$^{-1}$; [α]$_D$$^{25°}$=+50.2° (c=1, CHCl$_3$); pmr (CDCl$_3$) δ 10.3 (s, 1H), 7.7 (s, 1H), 6.3 (s, 2H), 4.6–3.8 (7H), 3.4–1.5 (7H), 1.3 (bs, 28H) and 0.9 (bt, 3H) ppm.

Anal. Calcd for C$_{28}$H$_{49}$ClN$_2$O$_4$: C, 65.53; H, 9.62; N, 5.46. Found: C, 65.20; H, 9.67; N, 5.60.

EXAMPLE 24

α-n-HEXADECANOYLOXYETHYLPILOCARPINE CHLORIDE mp 115°–119°; ir (KBr) 3040, 2920, 2840, 1745, 1560, 1470, 1175, 1140, 1100, 1015, 930 and 725 cm$^{-1}$; [α]$_D$$^{27°}$ = +46.7 (c= 1, CHCl$_3$); pmr (CDCl$_3$) δ 10.6 (s, 1H), 8.0 (s, 1H), 7.0 (q, 1H), 4.7–4.0 (7H), 3.6–1.5 (10H), 1.3 (bs, 28H) and 0.9 (bt, 3H), ppm.

Anal. Calcd for C$_{29}$H$_{51}$ClN$_2$O$_4$: C, 66.07; H, 9.75; N, 5.32. Found: C, 65.31; H, 9.62; N, 5.88.

EXAMPLE 25

α-n-DODECANOYLOXYETHYLPILOCARPINE CHLORIDE mp 96°–101°; ir (KBr) 3040, 2920, 2840, 1740, 1560, 1465, 1170, 1140, 1095, 1015 and 930 cm$^{-1}$; pmr (CDCl$_3$) δ 10.6 (s, 1H), 8.0 (s, 1H), 6.9 (q, 1H), 4.7–3.8 (7H), 3.5–1.5 (10H), 1.3 (bs, 20) and 0.9 (bt, 3H) ppm.

Anal. Calcd for C$_{25}$H$_{43}$ClN$_2$O$_4$: C, 63.74; H, 9.20; N, 5.95. Found: C, 63.07; H, 9.03; N, 7.06.

EXAMPLE 26

1-n-DODECANOYLOXYMETHYL-3-N,N-DIMETHYLCARBAMOYLPYRIDINIUM CHLORIDE

A mixture containing 1.66 g (0.01 mol) 3-N,N-dimethylcarbamoylpyridine and 2.49 g (0.01 mol) chloromethyl n-dodecanoate was heated at 90° for 3 hr. Trituration in anhydrous ether followed by filtration under nitrogen gave 2.6 g (0.006 mol), 60%, 1-n-dodecanoyloxymethyl-3,N,N-dimethylcarbamoylpyridinium chloride, mp 118°–120°; ir (KBr) 2900, 2840, 1710, 1460, 1380, 1320, 1250, 1155, 1100, 1030 and 680 cm$^{-1}$; pmr (CDCl$_3$) δ 9.5 (m, 2H), 8.5 (m, 2H), 7.0 (s, 2H), 3.1 (d, 6H), 2.4 (m, 2H), 1.3 (bs, 18H), and 0.9 (bt, 3H) ppm.

Anal. Calcd for $C_{21}H_{35}ClN_2O_4$: C, 60.78; H, 8.50; N, 6.75. Found: C, 60.62; H, 8.51; N, 6.99.

EXAMPLE 27

6,8-DICHLORO-α-[DIBUTYLAMINOMETHYL]-2-[3′,4′-DICHLOROPHENYL]-4-QUINOLINE-METHYL-N-BENZOYLOXYMETHYL-N,N-DIMETHYLGLYCINATE CHLORIDE (27)

6,8-Dichloro-α-[dibutylaminomethyl]-2-[3′,4′-dichlorophenyl]-4-quinolinemethyl-N,N-dimethylglycinate 1.05 g (0.00175 mol) was suspended in 7.86 g (0.0052 mol) chloromethyl benzoate. The suspension was stirred under nitrogen at ambient temperature overnite. The homogeneous suspension was titrated with heptane (30 ml) to give an oil. The mixture was further diluted with 100 ml anhydrous ether. The resulting suspension was stirred for several minutes then diluted to 200 ml with heptane and stirred for 1 hr. The suspension was filtered and the hygroscopic tan residue was dried in vacuo to give 0.95 g, 70%, 27, mp 110°–117°, ir (KBr) 3600, 3100, 2800, 2200 and 1750 cm$^{-1}$; pmr (CDCl$_3$) δ 2.0–0.65 (m, 14H), 3.2–2.8 (m, 6H), 3.8–3.2 (m, 6H), 6.35–6.6 (m, 1H), 6.95–6.6 (m, 1H) and 8.67–7.2 (m, 11H) ppm.

Anal. Calcd for $C_{37}H_{42}Cl_5N_3O_4 \cdot HCl$: C, 55.10; H, 5.37; N, 5.21. Found: C, 55.08; H, 5.27; N, 5.34.

EXAMPLE 28

3-[DIBUTYLAMINO]-1-[(2,6-bis-TRIFLUOROMETHYLPHENYL)-4-PYRIDYL]PROPANOL-N-BENZOYLOXYMETHYL-N,N-DIMETHYL-GLYCINATE CHLORIDE (28)

3-[Dibutylamino]-1-[(2,6-bis-trifluoromethylphenyl)-4-pyridyl]propanol-N,N-dimethylglycinate dihydrochloride 3.7 g (0.006 mol) was dissolved in a mixture of 50 ml dichloromethane and 100 ml tetrahydrofuran. Sodium methoxide 0.53 g (0.001 mol) dissolved in 2 ml water was added. After stirring for 10 minutes, the solvent was removed under reduced pressure. The residue was dissolved in 10 ml dichloromethane and 3.9 g (0.02 mol) chloromethyl benzoate was added. After stirring at ambient temperature overnite, 100 ml petroleum ether (30°–60°) was added. The solid formed was isolated by filtration and dried in vacuo to give 3.7 g (0.0045 mol), 75%, 28, mp 90°–92°.

Anal. Calcd for $C_{41}H_{46}Cl_2F_6N_3O_4$: C, 59.72; H, 5.85; N, 4.98. Found: C, 60.04; H, 6.11; N, 5.36.

EXAMPLE 29

BENZOYLOXYMETHYLPYRIDINIUM CHLORIDE (29)

A mixture containing 0.79 g (0.01 mol) pyridine and 1.7 g (0.01 mol) chloromethyl benzoate was allowed to react at ambient temperature for 24 hr. Trituration in anhydrous ether followed by filtration under nitrogen gave 1.2 g (0.005 mol), 50%, 29, mp 197°–199° (dec); ir (KBr) 3440, 3020, 1710, 1610, 1475, 1265, 1150, 1085, 870 and 700 cm$^{-1}$; pmr (D$_2$O) δ 7.0–10.0 (m, 10H) and 6.6 (s, 2H) ppm.

Anal. Calcd for $C_{13}H_{12}ClNO_2 \cdot \frac{1}{4}H_2O$: C, 61.42; H, 4.96; N, 5.51. Found: C, 61.48; H, 5.17; N, 5.40.

Following the procedure given in Example 29, the following benzoyloxymethylammonium salts were prepared:

EXAMPLE 30

1-BENZOYLOXYMETHYL-3-METHYLIMIDAZOLIUM CHLORIDE mp 149°–152°; ir (KBr) 3420, 3000, 1710, 1560, 1430, 110, 1160, 1090, 770 and 700 cm$^{-1}$; pmr (D$_2$O) δ 9.0 (bs, 1H), 7.0–8.2 (m, 7H), 6.3 (s, 2H) and 3.9 (s, 3H) ppm.

Anal. Calcd for $C_{12}H_{13}ClN_2O_2 \cdot \frac{1}{4}H_2O$: C, 56.03; H, 5.29; N, 10.89. Found: C, 56.17; H, 5.45; N, 10.66.

EXAMPLE 31

BENZOYLOXYMETHYLDIMETHYLBENZYLAMMONIUM CHLORIDE mp 159°–160° (dec), ir (KBr) 2980, 1710, 1435, 1270, 1100 and 700 cm$^{-1}$; pmr (CDCl$_3$) δ 7.2–8.2 (m, 10H), 6.2 (s, 2H), 5.4 (s, 2H) and 3.5 (s, 6H) ppm.

Anal. Calcd for $C_{17}H_{20}ClNO_2$: C, 66.77; H, 6.59; N, 4.58. Found: C, 66.56; H, 6.69; N, 4.77.

EXAMPLE 32

1-THIOACETYLOXYMETHYL-3-METHYLIMIDAZOLIUM CHLORIDE

To 0.7 g (8.52 millimoles) of 1-methylimidazole was added slowly and with cooling, 1.5 g of (16.2 millimoles) chloromethylthioacetate. The solution solidified in 10 minutes and was left stoppered at room temperature overnight.

Trituration of the reaction mixture with anhydrous THF and subsequent crystallization in the THF yields the crystalline, very hygroscopic product. The NMR spectrum was consistent with the title structure:

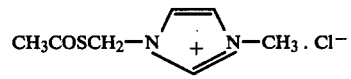

The quaternary salts described in the following table (Examples 33–50) are obtained by the same methods as described in Examples 1 to 32 above. The constituent symbols R, R$_1$,

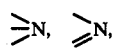

and Y are defined as above.

TABLE I $$R-CH-\overset{+}{N}\diagup \quad Y^{\ominus}$$
$$\underset{|}{O-\underset{\parallel}{C}-R_1}$$

$$R-CH-\overset{+}{N}\diagup \quad Y^{\ominus}$$
$$\underset{|}{O-\underset{\parallel}{C}-R_1}$$

| EX. | R | $R_1$ | $-N\diagup$ , $N=$ | Y |
|---|---|---|---|---|
| 33 | H— | phenyl | $-N(C_2H_5)_3$ | Cl |
| 34 | H— | phenyl | $-N(C_2H_5)_3$ | Br |
| 35 | $CH_3-$ | phenyl | $-N(C_2H_5)_3$ | Cl |
| 36 | H | $CH_3-$ | $-N(CH_2CH_2OCH_2CH_3)_3$ | Cl |
| 37 | H | phenyl | $-N(CH_2CH_2OCH_2CH_3)_3$ | Br |
| 38 | H— | phenyl | 3-carbamoylpyridinium | Cl |
| 39 | phenyl | phenyl | 3-(ethoxycarbonyl)pyridinium | Br |
| 40 | phenyl | phenyl-CH=CH— | 3-(ethoxycarbonyl)pyridinium | Cl |
| 41 | phenyl-CH=CH— | phenyl | $-N(CH_3)_3$ | Cl |
| 42 | H | $-C(CH_3)_3$ | $-N(CH_3)_3$ | Cl |
| 43 | H | $-C(CH_3)_3$ | 3-carbamoylpyridinium | Cl |

TABLE I-continued

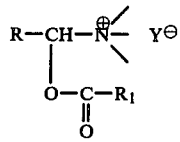

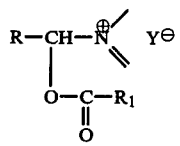

| EX. | R | R₁ | $-N\begin{smallmatrix}/\\\backslash\end{smallmatrix}\ \ N\begin{smallmatrix}/\\\backslash\end{smallmatrix}$ | Y |
|---|---|---|---|---|
| 44 | 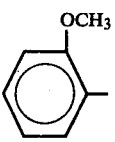 o-OCH₃ | 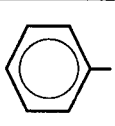 phenyl | 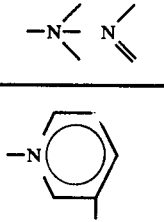 3-CONH₂-pyridyl | Br |
| 45 | 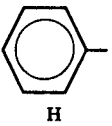 phenyl | 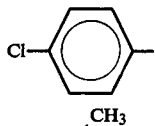 4-Cl-phenyl | $-N\begin{smallmatrix}CH_3\\-CH_3\\CH_3\end{smallmatrix}$ | Cl |
| 46 | H | $-C\begin{smallmatrix}CH_3\\-CH_3\\CH_3\end{smallmatrix}$ | 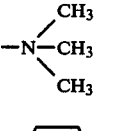 | Cl |
| 47 | 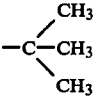 phenyl | 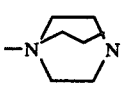 phenyl | 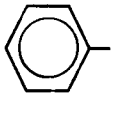<br>(Pilocarpine) Pilocarpine | Br |
| 48 | H | 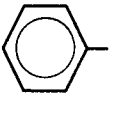 phenyl | 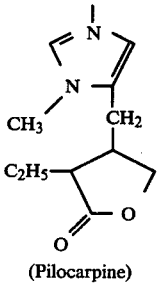 Pilocarpine | Cl |
| 49 | H | 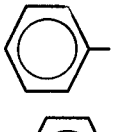 phenyl | $-N\begin{smallmatrix}CH_3\\-CH_3\\CH_2COOCH_3\end{smallmatrix}$ | Cl |
| 50 | H | 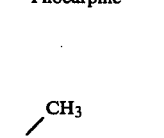$-C\begin{smallmatrix}CH_3\\-CH_3\\CH_3\end{smallmatrix}$ | $-N\begin{smallmatrix}C_2H_5\\-C_2H_5\\CH_2COOCH_2-\end{smallmatrix}$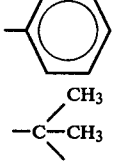 | Cl |

By following the previously described reaction schemes but substituting the appropriate generically and/or specifically described reactants and/or operating conditions, the following additional compounds as described in Table II below can be obtained.

TABLE II $$R-CH-\overset{\oplus}{\underset{|}{N}}\diagdown \quad Y^{\ominus} \qquad R-CH-\underset{|}{N}\diagdown \quad Y^{\ominus}$$
$$\underset{|}{X-C-R_1} \qquad \qquad \underset{|}{X-C-R_1}$$
$$\underset{O}{\|} \qquad \qquad \underset{O}{\|}$$

| Ex. | $-N\diagdown$ or $\diagup N\diagdown$ | R | $R_1$ | X | Y |
|---|---|---|---|---|---|
| 51 | $C_6H_5$-CH-N(piperazine)N-CH$_3$, with 4-Cl-phenyl (CHLORCYCLIZINE) | H— | —$C_6H_5$ | O | Cl, Br, I |
| 52 | " | H— | —C(CH$_3$)$_3$ | O | Cl, Br, I |
| 53 | " | H— | —$C_5H_{11}$ | O | Cl, Br, I |
| 54 | " | H— | —$C_{12}H_{25}$ | O | Cl, Br, I |
| 55 | " | CH$_3$— | —$C_6H_5$ | O | Cl, Br, I |
| 56 | " | CH$_3$— | —C(CH$_3$)$_3$ | O | Cl, Br, I |
| 57 | " | CH$_3$— | —$C_5H_{11}$ | O | Cl, Br, I |
| 58 | " | CH$_3$— | —$C_{12}H_{25}$ | O | Cl, Br, I |
| 59 | " | CCl$_3$— | —$C_6H_5$ | O | Cl, Br, I |
| 60 | " | CCl$_3$— | —C(CH$_3$)$_3$ | O | Cl, Br, I |
| 61 | " | CCl$_3$— | —$C_5H_{11}$ | O | Cl, Br, I |
| 62 | " | CCl$_3$— | —$C_{12}H_{25}$ | O | Cl, Br, I |
| 63 | " | $C_6H_5$— | —$C_6H_5$ | O | Cl, Br, I |
| 64 | " | $C_6H_5$— | —C(CH$_3$)$_3$ | O | Cl, Br, I |
| 65 | " | $C_6H_5$— | —$C_5H_{11}$ | O | Cl, Br, I |
| 66 | " | $C_6H_5$— | —$C_{12}H_{25}$ | O | Cl, Br, I |
| 67 | " | H— | —CH$_3$ | S | Cl, Br, I |
| 68 | phenyl-N(CH$_2$-thienyl)(CH$_2$CH$_2$-N(CH$_3$)$_2$) (METHAPHENILINE) | H— | —$C_6H_5$ | O | Cl, Br, I |
| 69 | " | H— | —C(CH$_3$)$_3$ | O | Cl, Br, I |
| 70 | " | H— | —$C_5H_{11}$ | O | Cl, Br, I |
| 71 | " | H— | —$C_{12}H_{25}$ | O | Cl, Br, I |
| 72 | " | CH$_3$— | —$C_6H_5$ | O | Cl, Br, I |
| 73 | " | CH$_3$— | —C(CH$_3$)$_3$ | O | Cl, Br, I |
| 74 | " | CH$_3$— | —$C_5H_{11}$ | O | Cl, Br, I |
| 75 | " | CH$_3$— | —$C_{12}H_{25}$ | O | Cl, Br, I |
| 76 | " | CCl$_3$— | —$C_6H_5$ | O | Cl, Br, I |

TABLE II-continued $$R-CH-\overset{\oplus}{N}\diagup \quad Y^{\ominus} \qquad R-CH-N\diagup \quad Y^{\ominus}$$
$$\underset{\|}{X-C-R_1} \qquad \qquad \underset{\|}{X-C-R_1}$$
$$\phantom{X-C}O \qquad \qquad \phantom{X-C}O$$

| Ex. | $\diagdown\!\!\!-N\diagup$ or $\diagdown\!\!\!N\diagup$ | R | $R_1$ | X | Y |
|---|---|---|---|---|---|
| 77 | " | CCl₃— | —C(CH₃)₃ | O | Cl, Br, I |
| 78 | " | CCl₃— | —C₅H₁₁ | O | Cl, Br, I |
| 79 | " | CCl₃— | —C₁₂H₂₅ | O | Cl, Br, I |
| 80 | " | C₆H₅— | —C₆H₅ | O | Cl, Br, I |
| 81 | " | C₆H₅— | —C(CH₃)₃ | O | Cl, Br, I |
| 82 | " | C₆H₅— | —C₅H₁₁ | O | Cl, Br, I |
| 83 | " | C₆H₅— | —C₁₂H₂₅ | O | Cl, Br, I |
| 84 | " | H— | —CH₃ | S | Cl, Br, I |
| 85 | " | H— | —C₆H₅ | O | Cl, Br, I |
| 86 | (PYRATHIAZINE) phenothiazine-N—CH₂—CH₂—N(pyrrolidine) | H— | —C(CH₃)₃ | O | Cl, Br, I |
| 87 | " | H— | —C₅H₁₁ | O | Cl, Br, I |
| 88 | " | H— | —C₁₂H₂₅ | O | Cl, Br, I |
| 89 | " | CH₃— | —C₆H₅ | O | Cl, Br, I |
| 90 | " | CH₃— | —C(CH₃)₃ | O | Cl, Br, I |
| 91 | " | CH₃— | —C₅H₁₁ | O | Cl, Br, I |
| 92 | " | CH₃— | —C₁₂H₂₅ | O | Cl, Br, I |
| 93 | " | CCl₃— | —C₆H₅ | O | Cl, Br, I |
| 94 | " | CCl₃— | —C(CH₃)₃ | O | Cl, Br, I |
| 95 | " | CCl₃— | —C₅H₁₁ | O | Cl, Br, I |
| 96 | " | CCl₃— | —C₁₂H₂₅ | O | Cl, Br, I |
| 97 | " | C₆H₅— | —C₆H₅ | O | Cl, Br, I |
| 98 | " | C₆H₅— | —C(CH₃)₃ | O | Cl, Br, I |
| 99 | " | C₆H₅— | —C₅H₁₁ | O | Cl, Br, I |
| 100 | " | C₆H₅— | —C₁₂H₂₅ | O | Cl, Br, I |
| 101 | " | H— | —CH₃ | S | Cl, Br, I |

TABLE II-continued $$R-CH-\overset{\oplus}{\underset{\underset{O}{X-C-R_1}}{N}}\diagup \quad Y^{\ominus} \qquad R-CH-\underset{\underset{O}{X-C-R_1}}{N}\diagup \quad Y^{\ominus}$$

| Ex. | $\diagdown N\diagup$ or $\diagdown N\diagup$ | R | $R_1$ | X | Y |
|---|---|---|---|---|---|
| 102 | (PYRILAMINE) 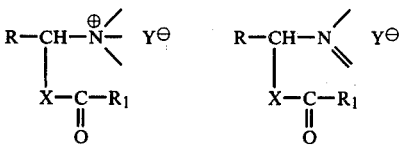 | H— | —$C_6H_5$ | O | Cl, Br, I |
| 103 | " | H— | —C(CH$_3$)$_3$ | O | Cl, Br, I |
| 104 | " | H— | —$C_5H_{11}$ | O | Cl, Br, I |
| 105 | " | H— | —$C_{12}H_{25}$ | O | Cl, Br, I |
| 106 | " | $CH_3$— | —$C_6H_5$ | O | Cl, Br, I |
| 107 | " | $CH_3$— | —C(CH$_3$)$_3$ | O | Cl, Br, I |
| 108 | " | $CH_3$— | —$C_5H_{11}$ | O | Cl, Br, I |
| 109 | " | $CH_3$— | —$C_{12}H_{25}$ | O | Cl, Br, I |
| 110 | " | $CCl_3$— | —$C_6H_5$ | O | Cl, Br, I |
| 111 | " | $CCl_3$— | —C(CH$_3$)$_3$ | O | Cl, Br, I |
| 112 | " | $CCl_3$— | —$C_5H_{11}$ | O | Cl, Br, I |
| 113 | " | $CCl_3$— | —$C_{12}H_{25}$ | O | Cl, Br, I |
| 114 | " | $C_6H_5$— | —$C_6H_5$ | O | Cl, Br, I |
| 115 | " | $C_6H_5$— | —C(CH$_3$)$_3$ | O | Cl, Br, I |
| 116 | " | $C_6H_5$— | —$C_5H_{11}$ | O | Cl, Br, I |
| 117 | " | $C_6H_5$— | —$C_{12}H_{25}$ | O | Cl, Br, I |
| 118 | " | H— | —$CH_3$ | S | Cl, Br, I |
| 119 | (CHLORPHENOXAMINE) 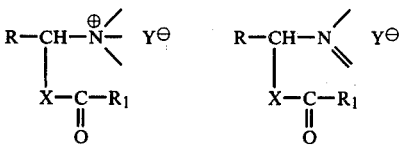 | H— | —$C_6H_5$ | O | Cl, Br, I |
| 120 | " | H— | —C(CH$_3$)$_3$ | O | Cl, Br, I |
| 121 | " | H— | —$C_5H_{11}$ | O | Cl, Br, I |
| 122 | " | H— | —$C_{12}H_{25}$ | O | Cl, Br, I |
| 123 | " | $CH_3$— | —$C_6H_5$ | O | Cl, Br, I |

TABLE II-continued $$R-CH-\overset{\oplus}{N}\diagup \quad Y^{\ominus} \qquad R-CH-N\diagup \quad Y^{\ominus}$$
$$\underset{O}{\overset{|}{X-C-R_1}} \qquad \underset{O}{\overset{|}{X-C-R_1}}$$

| Ex. | $\diagdown N$ or $\diagup N$ | R | $R_1$ | X | Y |
|---|---|---|---|---|---|
| 124 | " | $CH_3-$ | $-C(CH_3)_3$ | O | Cl, Br, I |
| 125 | " | $CH_3-$ | $-C_5H_{11}$ | O | Cl, Br, I |
| 126 | " | $CH_3-$ | $-C_{12}H_{25}$ | O | Cl, Br, I |
| 127 | " | $CCl_3-$ | $-C_6H_5$ | O | Cl, Br, I |
| 128 | " | $CCl_3-$ | $-C(CH_3)_3$ | O | Cl, Br, I |
| 129 | " | $CCl_3-$ | $-C_5H_{11}$ | O | Cl, Br, I |
| 130 | " | $CCl_3-$ | $-C_{12}H_{25}$ | O | Cl, Br, I |
| 131 | " | $C_6H_5-$ | $-C_6H_5$ | O | Cl, Br, I |
| 132 | " | $C_6H_5-$ | $-C(CH_3)_3$ | O | Cl, Br, I |
| 133 | " | $C_6H_5-$ | $-C_5H_{11}$ | O | Cl, Br, I |
| 134 | " | $C_6H_5-$ | $-C_{12}H_{25}$ | O | Cl, Br, I |
| 135 | " | $H-$ | $-CH_3$ | S | Cl, Br, I |
| 136 | (CLEMASTINE): $CH_3-C(C_6H_5)_2-CH_2-O-CH_2CH_2-$ [N-methylpyrrolidin-2-yl] | $H-$ | $-C_6H_5$ | O | Cl, Br, I |
| 137 | " | $H-$ | $-C(CH_3)_3$ | O | Cl, Br, I |
| 138 | " | $H-$ | $-C_5H_{11}$ | O | Cl, Br, I |
| 139 | " | $H-$ | $-C_{12}H_{25}$ | O | Cl, Br, I |
| 140 | " | $CH_3-$ | $-C_6H_5$ | O | Cl, Br, I |
| 141 | " | $CH_3-$ | $-C(CH_3)_3$ | O | Cl, Br, I |
| 142 | " | $CH_3-$ | $-C_5H_{11}$ | O | Cl, Br, I |
| 143 | " | $CH_3-$ | $-C_{12}H_{25}$ | O | Cl, Br, I |
| 144 | " | $CCl_3-$ | $-C_6H_5$ | O | Cl, Br, I |
| 145 | " | $CCl_3-$ | $-C(CH_3)_3$ | O | Cl, Br, I |
| 146 | " | $CCl_3-$ | $-C_5H_{11}$ | O | Cl, Br, I |
| 147 | " | $CCl_3-$ | $-C_{12}H_{25}$ | O | Cl, Br, I |
| 148 | " | $C_6H_5-$ | $-C_6H_5$ | O | Cl, Br, I |
| 149 | " | $C_6H_5-$ | $-C(CH_3)_3$ | O | Cl, Br, I |
| 150 | " | $C_6H_5-$ | $-C_5H_{11}$ | O | Cl, Br, I |
| 151 | " | $C_6H_5-$ | $-C_{12}H_{25}$ | O | Cl, Br, I |
| 152 | " | $H-$ | $-CH_3$ | S | Cl, Br, I |

TABLE II-continued $$\underset{\underset{O}{X-C-R_1}}{R-CH-\overset{\oplus}{N}\diagdown}\; Y^{\ominus} \qquad \underset{\underset{O}{X-C-R_1}}{R-CH-N\diagdown}\; Y^{\ominus}$$

| Ex. | −N⟨ or N= | R | R$_1$ | X | Y |
|---|---|---|---|---|---|
| 153 | (DIPHENYLPRALINE) [diphenyl-CHO-(N-methylpiperidin-4-yl)] | H— | —C$_6$H$_5$ | O | Cl, Br, I |
| 154 | " | H— | —C(CH$_3$)$_3$ | O | Cl, Br, I |
| 155 | " | H— | —C$_5$H$_{11}$ | O | Cl, Br, I |
| 156 | " | H— | —C$_{12}$H$_{25}$ | O | Cl, Br, I |
| 157 | " | CH$_3$— | —C$_6$H$_5$ | O | Cl, Br, I |
| 158 | " | CH$_3$— | —C(CH$_3$)$_3$ | O | Cl, Br, I |
| 159 | " | CH$_3$— | —C$_5$H$_{11}$ | O | Cl, Br, I |
| 160 | " | CH$_3$— | —C$_{12}$H$_{25}$ | O | Cl, Br, I |
| 161 | " | CCl$_3$— | —C$_6$H$_5$ | O | Cl, Br, I |
| 162 | " | CCl$_3$— | —C(CH$_3$)$_3$ | O | Cl, Br, I |
| 163 | " | CCl$_3$— | —C$_5$H$_{11}$ | O | Cl, Br, I |
| 164 | " | CCl$_3$— | —C$_{12}$H$_{25}$ | O | Cl, Br, I |
| 165 | " | C$_6$H$_5$— | —C$_6$H$_5$ | O | Cl, Br, I |
| 166 | " | C$_6$H$_5$— | —C(CH$_3$)$_3$ | O | Cl, Br, I |
| 167 | " | C$_6$H$_5$— | —C$_5$H$_{11}$ | O | Cl, Br, I |
| 168 | " | C$_6$H$_5$— | —C$_{12}$H$_{25}$ | O | Cl, Br, I |
| 169 | " | H— | —CH$_3$ | S | Cl, Br, I |
| 170 | (DOXYLAMINE) [CH$_3$-C(C$_6$H$_5$)$_2$-O-CH$_2$CH$_2$-N(CH$_3$)$_2$] | H— | —C$_6$H$_5$ | O | Cl, Br, I |
| 171 | " | H— | —C(CH$_3$)$_3$ | O | Cl, Br, I |
| 172 | " | H— | —C$_5$H$_{11}$ | O | Cl, Br, I |
| 173 | " | H— | —C$_{12}$H$_{25}$ | O | Cl, Br, I |
| 174 | " | CH$_3$— | —C$_6$H$_5$ | O | Cl, Br, I |
| 175 | " | CH$_3$— | —C(CH$_3$)$_3$ | O | Cl, Br, I |
| 176 | " | CH$_3$— | —C$_5$H$_{11}$ | O | Cl, Br, I |

TABLE II-continued $$R-CH-\overset{\oplus}{\underset{|}{N}}\diagup \quad Y^{\ominus} \qquad R-CH-N\diagup \quad Y^{\ominus}$$
$$\underset{|}{X-C-R_1} \qquad \underset{|}{X-C-R_1}$$
$$\underset{O}{\parallel} \qquad \underset{O}{\parallel}$$

| Ex. | $\diagdown$N or $\diagdown$N | R | $R_1$ | X | Y |
|---|---|---|---|---|---|
| 177 | " | $CH_3-$ | $-C_{12}H_{25}$ | O | Cl, Br, I |
| 178 | " | $CCl_3-$ | $-C_6H_5$ | O | Cl, Br, I |
| 179 | " | $CCl_3-$ | $-C(CH_3)_3$ | O | Cl, Br, I |
| 180 | " | $CCl_3-$ | $-C_5H_{11}$ | O | Cl, Br, I |
| 181 | " | $CCl_3-$ | $-C_{12}H_{25}$ | O | Cl, Br, I |
| 182 | " | $C_6H_5-$ | $-C_6H_5$ | O | Cl, Br, I |
| 183 | " | $C_6H_5-$ | $-C(CH_3)_3$ | O | Cl, Br, I |
| 184 | " | $C_6H_5-$ | $-C_5H_{11}$ | O | Cl, Br, I |
| 185 | " | $C_6H_5-$ | $-C_{12}H_{25}$ | O | Cl, Br, I |
| 186 | " | $H-$ | $-CH_3$ | S | Cl, Br, I |
| 187 | (CYCLIRAMINE) | $H-$ | $-C_6H_5$ | O | Cl, Br, I |
| 188 | " | $H-$ | $-C(CH_3)_3$ | O | Cl, Br, I |
| 189 | " | $H-$ | $-C_5H_{11}$ | O | Cl, Br, I |
| 190 | " | $H-$ | $-C_{12}H_{25}$ | O | Cl, Br, I |
| 191 | " | $CH_3-$ | $-C_6H_5$ | O | Cl, Br, I |
| 192 | " | $CH_3-$ | $-C(CH_3)_3$ | O | Cl, Br, I |
| 193 | " | $CH_3-$ | $-C_5H_{11}$ | O | Cl, Br, I |
| 194 | " | $CH_3-$ | $-C_{12}H_{25}$ | O | Cl, Br, I |
| 195 | " | $CCl_3-$ | $-C_6H_5$ | O | Cl, Br, I |
| 196 | " | $CCl_3-$ | $-C(CH_3)_3$ | O | Cl, Br, I |
| 197 | " | $CCl_3-$ | $-C_5H_{11}$ | O | Cl, Br, I |
| 198 | " | $CCl_3-$ | $-C_{12}H_{25}$ | O | Cl, Br, I |
| 199 | " | $C_6H_5-$ | $-C_6H_5$ | O | Cl, Br, I |
| 200 | " | $C_6H_5-$ | $-C(CH_3)_3$ | O | Cl, Br, I |
| 201 | " | $C_6H_5-$ | $-C_5H_{11}$ | O | Cl, Br, I |
| 202 | " | $C_6H_5-$ | $-C_{12}H_{25}$ | O | Cl, Br, I |
| 203 | " | $H-$ | $-CH_3$ | S | Cl, Br, I |

TABLE II-continued $$R-CH-\overset{\oplus}{\underset{|}{N}}\diagup \quad Y^{\ominus} \qquad R-CH-N\diagup \quad Y^{\ominus}$$
$$\underset{\underset{O}{\parallel}}{X-C-R_1} \qquad \qquad \underset{\underset{O}{\parallel}}{X-C-R_1}$$

| Ex. | >N or >N= | R | R₁ | X | Y |
|---|---|---|---|---|---|
| 204 | (PHENINDAMINE) CH₃—N... C₆H₅ | H— | —C₆H₅ | O | Cl, Br, I |
| 205 | " | H— | —C(CH₃)₃ | O | Cl, Br, I |
| 206 | " | H— | —C₅H₁₁ | O | Cl, Br, I |
| 207 | " | H— | —C₁₂H₂₅ | O | Cl, Br, I |
| 208 | " | CH₃— | —C₆H₅ | O | Cl, Br, I |
| 209 | " | CH₃— | —C(CH₃)₃ | O | Cl, Br, I |
| 210 | " | CH₃— | —C₅H₁₁ | O | Cl, Br, I |
| 211 | " | CH₃— | —C₁₂H₂₅ | O | Cl, Br, I |
| 212 | " | CCl₃— | —C₆H₅ | O | Cl, Br, I |
| 213 | " | CCl₃— | —C(CH₃)₃ | O | Cl, Br, I |
| 214 | " | CCl₃— | —C₅H₁₁ | O | Cl, Br, I |
| 215 | " | CCl₃— | —C₁₂H₂₅ | O | Cl, Br, I |
| 216 | " | C₆H₅— | —C₆H₅ | O | Cl, Br, I |
| 217 | " | C₆H₅— | —C(CH₃)₃ | O | Cl, Br, I |
| 218 | " | C₆H₅— | —C₅H₁₁ | O | Cl, Br, I |
| 219 | " | C₆H₅— | —C₁₂H₂₅ | O | Cl, Br, I |
| 220 | " | H— | —CH₃ | S | Cl, Br, I |
| 221 | (CYCLIZINE) C₆H₅–CH–N(piperazine)N—CH₃ / C₆H₅ | H— | —C₆H₅ | O | Cl, Br, I |
| 222 | " | H— | —C(CH₃)₃ | O | Cl, Br, I |
| 223 | " | H— | —C₅H₁₁ | O | Cl, Br, I |
| 224 | " | H— | —C₁₂H₂₅ | O | Cl, Br, I |
| 225 | " | CH₃— | —C₆H₅ | O | Cl, Br, I |
| 226 | " | CH₃— | —C(CH₃)₃ | O | Cl, Br, I |
| 227 | " | CH₃— | —C₅H₁₁ | O | Cl, Br, I |
| 228 | " | CH₃— | —C₁₂H₂₅ | O | Cl, Br, I |
| 229 | " | CCl₃— | —C₆H₅ | O | Cl, Br, I |
| 230 | " | CCl₃— | —C(CH₃)₃ | O | Cl, Br, I |
| 231 | " | CCl₃— | —C₅H₁₁ | O | Cl, Br, I |
| 232 | " | CCl₃— | —C₁₂H₂₅ | O | Cl, Br, I |

TABLE II-continued $$R-CH-\overset{\oplus}{N}\diagdown\quad Y^\ominus \qquad R-CH-N\diagdown\quad Y^\ominus$$
$$\underset{\underset{O}{\overset{\|}{X-C-R_1}}}{|} \qquad \underset{\underset{O}{\overset{\|}{X-C-R_1}}}{|}$$

| Ex. | $\diagdown N$ or $\diagdown N$ | R | $R_1$ | X | Y |
|---|---|---|---|---|---|
| 233 | " | $C_6H_5-$ | $-C_6H_5$ | O | Cl, Br, I |
| 234 | " | $C_6H_5-$ | $-C(CH_3)_3$ | O | Cl, Br, I |
| 235 | " | $C_6H_5-$ | $-C_5H_{11}$ | O | Cl, Br, I |
| 236 | " | $C_6H_5-$ | $-C_{12}H_{25}$ | O | Cl, Br, I |
| 237 | " | $H-$ | $-CH_3$ | S | Cl, Br, I |
| 238 | Ph-CH(OCOCH$_3$)-CH(CH$_3$)-N(C$_2$H$_5$)(CH$_3$) (ETAFEDRINE ACETATE) | $H-$ | $-C_6H_5$ | O | Cl, Br, I |
| 239 | " | $H-$ | $-C(CH_3)_3$ | O | Cl, Br, I |
| 240 | " | $H-$ | $-C_5H_{11}$ | O | Cl, Br, I |
| 241 | " | $H-$ | $-C_{12}H_{25}$ | O | Cl, Br, I |
| 242 | " | $CH_3-$ | $-C_6H_5$ | O | Cl, Br, I |
| 243 | " | $CH_3-$ | $-C(CH_3)_3$ | O | Cl, Br, I |
| 244 | " | $CH_3-$ | $-C_5H_{11}$ | O | Cl, Br, I |
| 245 | " | $CH_3-$ | $-C_{12}H_{25}$ | O | Cl, Br, I |
| 246 | " | $CCl_3-$ | $-C_6H_5$ | O | Cl, Br, I |
| 247 | " | $CCl_3-$ | $-C(CH_3)_3$ | O | Cl, Br, I |
| 248 | " | $CCl_3-$ | $-C_5H_{11}$ | O | Cl, Br, I |
| 249 | " | $CCl_3-$ | $-C_{12}H_{25}$ | O | Cl, Br, I |
| 250 | " | $C_6H_5-$ | $-C_6H_5$ | O | Cl, Br, I |
| 251 | " | $C_6H_5-$ | $-C(CH_3)_3$ | O | Cl, Br, I |
| 252 | " | $C_6H_5-$ | $-C_5H_{11}$ | O | Cl, Br, I |
| 253 | " | $C_6H_5-$ | $-C_{12}H_{25}$ | O | Cl, Br, I |
| 254 | " | $H-$ | $-CH_3$ | S | Cl, Br, I |
| 255 | Ph-CH$_2$-CH(CH$_3$)-N(CH$_3$)-CH$_2$-Ph (BENZPHETAMINE) | $H-$ | $-C_6H_5$ | O | Cl, Br, I |
| 256 | " | $H-$ | $-C(CH_3)_3$ | O | Cl, Br, I |
| 257 | " | $H-$ | $-C_5H_{11}$ | O | Cl, Br, I |
| 258 | " | $H-$ | $-C_{12}H_{25}$ | O | Cl, Br, I |
| 259 | " | $CH_3-$ | $-C_6H_5$ | O | Cl, Br, I |
| 260 | " | $CH_3-$ | $-C(CH_3)_3$ | O | Cl, Br, I |
| 261 | " | $CH_3-$ | $-C_5H_{11}$ | O | Cl, Br, I |

4,160,099

TABLE II-continued $$R-CH-\overset{\oplus}{N}\diagup \quad Y^{\ominus} \qquad R-CH-N\diagup \quad Y^{\ominus}$$
$$\underset{\underset{O}{\|}}{X-C-R_1} \qquad \underset{\underset{O}{\|}}{X-C-R_1}$$

| Ex. | $\diagdown N$ or $\diagdown N\diagup\!\!\!\diagup$ | R | $R_1$ | X | Y |
|---|---|---|---|---|---|
| 262 | " | $CH_3-$ | $-C_{12}H_{25}$ | O | Cl, Br, I |
| 263 | " | $CCl_3-$ | $-C_6H_5$ | O | Cl, Br, I |
| 264 | " | $CCl_3-$ | $-C(CH_3)_3$ | O | Cl, Br, I |
| 265 | " | $CCl_3-$ | $-C_5H_{11}$ | O | Cl, Br, I |
| 266 | " | $CCl_3-$ | $-C_{12}H_{25}$ | O | Cl, Br, I |
| 267 | " | $C_6H_5-$ | $-C_6H_5$ | O | Cl, Br, I |
| 268 | " | $C_6H_5-$ | $-C(CH_3)_3$ | O | Cl, Br, I |
| 269 | " | $C_6H_5-$ | $-C_5H_{11}$ | O | Cl, Br, I |
| 270 | " | $C_6H_5-$ | $-C_{12}H_{25}$ | O | Cl, Br, I |
| 271 | " | $H-$ | $-CH_3$ | S | Cl, Br, I |
| 272 | (DIETHYLPROPION) | $H-$ | $-C_6H_5$ | O | Cl, Br, I |
| 273 | " | $H-$ | $-C(CH_3)_3$ | O | Cl, Br, I |
| 274 | " | $H-$ | $-C_5H_{11}$ | O | Cl, Br, I |
| 275 | " | $H-$ | $-C_{12}H_{25}$ | O | Cl, Br, I |
| 276 | " | $CH_3-$ | $-C_6H_5$ | O | Cl, Br, I |
| 277 | " | $CH_3-$ | $-C(CH_3)_3$ | O | Cl, Br, I |
| 278 | " | $CH_3-$ | $-C_5H_{11}$ | O | Cl, Br, I |
| 279 | " | $CH_3-$ | $-C_{12}H_{25}$ | O | Cl, Br, I |
| 280 | " | $CCl_3-$ | $-C_6H_5$ | O | Cl, Br, I |
| 281 | " | $CCl_3-$ | $-C(CH_3)_3$ | O | Cl, Br, I |
| 282 | " | $CCl_3-$ | $-C_5H_{11}$ | O | Cl, Br, I |
| 283 | " | $CCl_3-$ | $-C_{12}H_{25}$ | O | Cl, Br, I |
| 284 | " | $C_6H_5-$ | $-C_6H_5$ | O | Cl, Br, I |
| 285 | " | $C_6H_5-$ | $-C(CH_3)_3$ | O | Cl, Br, I |
| 286 | " | $C_6H_5-$ | $-C_5H_{11}$ | O | Cl, Br, I |
| 287 | " | $C_6H_5-$ | $-C_{12}H_{25}$ | O | Cl, Br, I |
| 288 | " | $H-$ | $-CH_3$ | S | Cl, Br, I |
| 289 | (PHENDIMETRAZINE) | $H-$ | $-C_6H_5$ | O | Cl, Br, I |
| 290 | " | $H-$ | $-C(CH_3)_3$ | O | Cl, Br, I |

TABLE II-continued

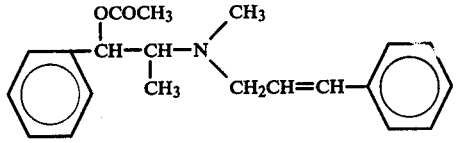

| Ex. | ⟩N or ⟩N | R | R₁ | X | Y |
|---|---|---|---|---|---|
| 291 | " | H— | —C$_5$H$_{11}$ | O | Cl, Br, I |
| 292 | " | H— | —C$_{12}$H$_{25}$ | O | Cl, Br, I |
| 293 | " | CH$_3$— | —C$_6$H$_5$ | O | Cl, Br, I |
| 294 | " | CH$_3$— | —C(CH$_3$)$_3$ | O | Cl, Br, I |
| 295 | " | CH$_3$— | —C$_5$H$_{11}$ | O | Cl, Br, I |
| 296 | " | CH$_3$— | —C$_{12}$H$_{25}$ | O | Cl, Br, I |
| 297 | " | CCl$_3$— | —C$_6$H$_5$ | O | Cl, Br, I |
| 298 | " | CCl$_3$— | —C(CH$_3$)$_3$ | O | Cl, Br, I |
| 299 | " | CCl$_3$— | —C$_5$H$_{11}$ | O | Cl, Br, I |
| 300 | " | CCl$_3$— | —C$_{12}$H$_{25}$ | O | Cl, Br, I |
| 301 | " | C$_6$H$_5$— | —C$_6$H$_5$ | O | Cl, Br, I |
| 302 | " | C$_6$H$_5$— | —C(CH$_3$)$_3$ | O | Cl, Br, I |
| 303 | " | C$_6$H$_5$— | —C$_5$H$_{11}$ | O | Cl, Br, I |
| 304 | " | C$_6$H$_5$— | —C$_{12}$H$_{25}$ | O | Cl, Br, I |
| 305 | " | H— | —CH$_3$ | S | Cl, Br, I |
| 306 | (CINNAMEDRINE ACETATE) | H— | —C$_6$H$_5$ | O | Cl, Br, I |
| 307 | " | H— | —C(CH$_3$)$_3$ | O | Cl, Br, I |
| 308 | " | H— | —C$_5$H$_{11}$ | O | Cl, Br, I |
| 309 | " | H— | —C$_{12}$H$_{25}$ | O | Cl, Br, I |
| 310 | " | CH$_3$— | —C$_6$H$_5$ | O | Cl, Br, I |
| 311 | " | CH$_3$— | —C(CH$_3$)$_3$ | O | Cl, Br, I |
| 312 | " | CH$_3$— | —C$_5$H$_{11}$ | O | Cl, Br, I |
| 313 | " | CH$_3$— | —C$_{12}$H$_{25}$ | O | Cl, Br, I |
| 314 | " | CCl$_3$— | —C$_6$H$_5$ | O | Cl, Br, I |
| 315 | " | CCl$_3$— | —C(CH$_3$)$_3$ | O | Cl, Br, I |
| 316 | " | CCl$_3$— | —C$_5$H$_{11}$ | O | Cl, Br, I |
| 317 | " | CCl$_3$— | —C$_{12}$H$_{25}$ | O | Cl, Br, I |
| 318 | " | C$_6$H$_5$— | —C$_6$H$_5$ | O | Cl, Br, I |
| 319 | " | C$_6$H$_5$— | —C(CH$_3$)$_3$ | O | Cl, Br, I |
| 320 | " | C$_6$H$_5$— | —C$_5$H$_{11}$ | O | Cl, Br, I |
| 321 | " | C$_6$H$_5$— | —C$_{12}$H$_{25}$ | O | Cl, Br, I |
| 322 | " | H— | —CH$_3$ | S | Cl, Br, I |

TABLE II-continued $$R-CH-\overset{+}{N}\diagup \quad Y^{\ominus} \qquad R-CH-N\diagup \quad Y^{\ominus}$$
$$\underset{O}{\overset{|}{X-C-R_1}} \qquad\qquad \underset{O}{\overset{|}{X-C-R_1}}$$

| Ex. | $\diagdown N$ or $\diagdown N\diagup\!\!\!\!\!\!\!/$ | R | $R_1$ | X | Y |
|---|---|---|---|---|---|
| 323 | (PIPEROXAN) benzodioxane-CH₂-N-piperidine | H— | —C₆H₅ | O | Cl, Br, I |
| 324 | " | H— | —C(CH₃)₃ | O | Cl, Br, I |
| 325 | " | H— | —C₅H₁₁ | O | Cl, Br, I |
| 326 | " | H— | —C₁₂H₂₅ | O | Cl, Br, I |
| 327 | " | CH₃— | —C₆H₅ | O | Cl, Br, I |
| 328 | " | CH₃— | —C(CH₃)₃ | O | Cl, Br, I |
| 329 | " | CH₃— | —C₅H₁₁ | O | Cl, Br, I |
| 330 | " | CH₃— | —C₁₂H₂₅ | O | Cl, Br, I |
| 331 | " | CCl₃— | —C₆H₅ | O | Cl, Br, I |
| 332 | " | CCl₃— | —C(CH₃)₃ | O | Cl, Br, I |
| 333 | " | CCl₃— | —C₅H₁₁ | O | Cl, Br, I |
| 334 | " | CCl₃— | —C₁₂H₂₅ | O | Cl, Br, I |
| 335 | " | C₆H₅— | —C₆H₅ | O | Cl, Br, I |
| 336 | " | C₆H₅— | —C(CH₃)₃ | O | Cl, Br, I |
| 337 | " | C₆H₅— | —C₅H₁₁ | O | Cl, Br, I |
| 338 | " | C₆H₅— | —C₁₂H₂₅ | O | Cl, Br, I |
| 339 | " | H— | —CH₃ | S | Cl, Br, I |
| 340 | (AZAPETINE) dibenzazepine N—CH₂CH=CH₂ | H— | —C₆H₅ | O | Cl, Br, I |
| 341 | " | H— | —C(CH₃)₃ | O | Cl, Br, I |
| 342 | " | H— | —C₅H₁₁ | O | Cl, Br, I |
| 343 | " | H— | —C₁₂H₂₅ | O | Cl, Br, I |
| 344 | " | CH₃— | —C₆H₅ | O | Cl, Br, I |
| 345 | " | CH₃— | —C(CH₃)₃ | O | Cl, Br, I |
| 346 | " | CH₃— | —C₅H₁₁ | O | Cl, Br, I |
| 347 | " | CH₃— | —C₁₂H₂₅ | O | Cl, Br, I |
| 348 | " | CCl₃— | —C₆H₅ | O | Cl, Br, I |
| 349 | " | CCl₃— | —C(CH₃)₃ | O | Cl, Br, I |

4,160,099

TABLE II-continued $$R-CH-\overset{\oplus}{\underset{X-C-R_1}{N}}\diagdown \quad Y^{\ominus} \qquad R-CH-\underset{X-C-R_1}{N}\diagdown \quad Y^{\ominus}$$
$$\phantom{R-CH-}\overset{\|}{O} \qquad \phantom{R-CH-}\overset{\|}{O}$$

| Ex. | $\diagdown N$ or $\diagdown N$ | R | $R_1$ | X | Y |
|---|---|---|---|---|---|
| 350 | " | $CCl_3-$ | $-C_5H_{11}$ | O | Cl, Br, I |
| 351 | " | $CCl_3-$ | $-C_{12}H_{25}$ | O | Cl, Br, I |
| 352 | " | $C_6H_5-$ | $-C_6H_5$ | O | Cl, Br, I |
| 353 | " | $C_6H_5-$ | $-C(CH_3)_3$ | O | Cl, Br, I |
| 354 | " | $C_6H_5-$ | $-C_5H_{11}$ | O | Cl, Br, I |
| 355 | " | $C_6H_5-$ | $-C_{12}H_{25}$ | O | Cl, Br, I |
| 356 | " | $H-$ | $-CH_3$ | S | Cl, Br, I |
| 357 | " | $H-$ | $-C_6H_5$ | O | Cl, Br, I |
| | (ARECOLINE) | | | | |
| 358 | " | $H-$ | $-C(CH_3)_3$ | O | Cl, Br, I |
| 359 | " | $H-$ | $-C_5H_{11}$ | O | Cl, Br, I |
| 360 | " | $H-$ | $-C_{12}H_{25}$ | O | Cl, Br, I |
| 361 | " | $CH_3-$ | $-C_6H_5$ | O | Cl, Br, I |
| 362 | " | $CH_3-$ | $-C(CH_3)_3$ | O | Cl, Br, I |
| 363 | " | $CH_3-$ | $-C_5H_{11}$ | O | Cl, Br, I |
| 364 | " | $CH_3-$ | $-C_{12}H_{25}$ | O | Cl, Br, I |
| 365 | " | $CCl_3-$ | $-C_6H_5$ | O | Cl, Br, I |
| 366 | " | $CCl_3-$ | $-C(CH_3)_3$ | O | Cl, Br, I |
| 367 | " | $CCl_3-$ | $-C_5H_{11}$ | O | Cl, Br, I |
| 368 | " | $CCl_3-$ | $-C_{12}H_{25}$ | O | Cl, Br, I |
| 369 | " | $C_6H_5-$ | $-C_6H_5$ | O | Cl, Br, I |
| 370 | " | $C_6H_5-$ | $-C(CH_3)_3$ | O | Cl, Br, I |
| 371 | " | $C_6H_5-$ | $-C_5H_{11}$ | O | Cl, Br, I |
| 372 | " | $C_6H_5-$ | $-C_{12}H_{25}$ | O | Cl, Br, I |
| 373 | " | $H-$ | $-CH_3$ | S | Cl, Br, I |
| 374 | " | $H-$ | $-C_6H_5$ | O | Cl, Br, I |
| | (PHYSOSTIGMINE) | | | | |
| 375 | " | $H-$ | $-C(CH_3)_3$ | O | Cl, Br, I |
| 376 | " | $H-$ | $-C_5H_{11}$ | O | Cl, Br, I |
| 377 | " | $H-$ | $-C_{12}H_{25}$ | O | Cl, Br, I |
| 378 | " | $CH_3-$ | $-C_6H_5$ | O | Cl, Br, I |

TABLE II-continued $$R-CH-\overset{\oplus}{N}\diagdown \quad Y^{\ominus} \qquad R-CH-N\diagdown \quad Y^{\ominus}$$
$$\underset{O}{\overset{|}{X-C-R_1}} \qquad \underset{O}{\overset{|}{X-C-R_1}}$$

| Ex. | $\diagdown\!\!\!-\!\!\!N\diagdown$ or $\diagdown\!\!\!N\!\!\!\diagup\!\!\!\diagup$ | R | $R_1$ | X | Y |
|---|---|---|---|---|---|
| 379 | " | $CH_3-$ | $-C(CH_3)_3$ | O | Cl, Br, I |
| 380 | " | $CH_3-$ | $-C_5H_{11}$ | O | Cl, Br, I |
| 381 | " | $CH_3-$ | $-C_{12}H_{25}$ | O | Cl, Br, I |
| 382 | " | $CCl_3-$ | $-C_6H_5$ | O | Cl, Br, I |
| 383 | " | $CCl_3-$ | $-C(CH_3)_3$ | O | Cl, Br, I |
| 384 | " | $CCl_3-$ | $-C_5H_{11}$ | O | Cl, Br, I |
| 385 | " | $CCl_3-$ | $-C_{12}H_{25}$ | O | Cl, Br, I |
| 386 | " | $C_6H_5-$ | $-C_6H_5$ | O | Cl, Br, I |
| 387 | " | $C_6H_5-$ | $-C(CH_3)_3$ | O | Cl, Br, I |
| 388 | " | $C_6H_5-$ | $-C_5H_{11}$ | O | Cl, Br, I |
| 389 | " | $C_6H_5-$ | $-C_{12}H_{25}$ | O | Cl, Br, I |
| 390 | " | $H-$ | $-CH_3$ | S | Cl, Br, I |
| 391 | (PROPIONYL ATROPINE) $C_2H_5COOCH_2\!-\!\underset{C_6H_5}{\overset{|}{CH}}\!-\!\overset{O}{\overset{\|}{C}}\!-\!O\!-\!CH\diagup\overset{CH_2-CH}{\underset{CH_2-CH}{\diagdown}}\overset{CH_2}{\underset{CH_2}{\diagdown}}N\!-\!CH_3$ | $H-$ | $-C_6H_5$ | O | Cl, Br, I |
| 392 | " | $H-$ | $-C(CH_3)_3$ | O | Cl, Br, I |
| 393 | " | $H-$ | $-C_5H_{11}$ | O | Cl, Br, I |
| 394 | " | $H-$ | $-C_{12}H_{25}$ | O | Cl, Br, I |
| 395 | " | $CH_3-$ | $-C_6H_5$ | O | Cl, Br, I |
| 396 | " | $CH_3-$ | $-C(CH_3)_3$ | O | Cl, Br, I |
| 397 | " | $CH_3-$ | $-C_5H_{11}$ | O | Cl, Br, I |
| 398 | " | $CH_3-$ | $-C_{12}H_{25}$ | O | Cl, Br, I |
| 399 | " | $CCl_3-$ | $-C_6H_5$ | O | Cl, Br, I |
| 400 | " | $CCl_3-$ | $-C(CH_3)_3$ | O | Cl, Br, I |
| 401 | " | $CCl_3-$ | $-C_5H_{11}$ | O | Cl, Br, I |
| 402 | " | $CCl_3-$ | $-C_{12}H_{25}$ | O | Cl, Br, I |
| 403 | " | $C_6H_5-$ | $-C_6H_5$ | O | Cl, Br, I |
| 404 | " | $C_6H_5-$ | $-C(CH_3)_3$ | O | Cl, Br, I |
| 405 | " | $C_6H_5-$ | $-C_5H_{11}$ | O | Cl, Br, I |
| 406 | " | $C_6H_5-$ | $-C_{12}H_{25}$ | O | Cl, Br, I |
| 407 | " | $H-$ | $-CH_3$ | S | Cl, Br, I |
| 408 | (ADIPHININE) $\underset{C_6H_5}{\overset{C_6H_5}{\diagdown}}CH\!-\!COOCH_2CH_2\!-\!N\overset{C_2H_5}{\underset{C_2H_5}{\diagup}}$ | $H-$ | $-C_6H_5$ | O | Cl, Br, I |

TABLE II-continued $$R-CH-\overset{\oplus}{N}\diagdown \quad Y^{\ominus} \qquad R-CH-N\diagdown \quad Y^{\ominus}$$
$$\underset{O}{\overset{|}{X-C-R_1}} \qquad \underset{O}{\overset{|}{X-C-R_1}}$$

| Ex. | $\diagdown\!\!\!-N$ or $\diagdown\!\!\!N$ | R | $R_1$ | X | Y |
|---|---|---|---|---|---|
| 409 | " | H— | $-C(CH_3)_3$ | O | Cl, Br, I |
| 410 | " | H— | $-C_5H_{11}$ | O | Cl, Br, I |
| 411 | " | H— | $-C_{12}H_{25}$ | O | Cl, Br, I |
| 412 | " | $CH_3-$ | $-C_6H_5$ | O | Cl, Br, I |
| 413 | " | $CH_3-$ | $-C(CH_3)_3$ | O | Cl, Br, I |
| 414 | " | $CH_3-$ | $-C_5H_{11}$ | O | Cl, Br, I |
| 415 | " | $CH_3-$ | $-C_{12}H_{25}$ | O | Cl, Br, I |
| 416 | " | $CCl_3-$ | $-C_6H_5$ | O | Cl, Br, I |
| 417 | " | $CCl_3-$ | $-C(CH_3)_3$ | O | Cl, Br, I |
| 418 | " | $CCl_3-$ | $-C_5H_{11}$ | O | Cl, Br, I |
| 419 | " | $CCl_3-$ | $-C_{12}H_{25}$ | O | Cl, Br, I |
| 420 | " | $C_6H_5-$ | $-C_6H_5$ | O | Cl, Br, I |
| 421 | " | $C_6H_5-$ | $-C(CH_3)_3$ | O | Cl, Br, I |
| 422 | " | $C_6H_5-$ | $-C_5H_{11}$ | O | Cl, Br, I |
| 423 | " | $C_6H_5-$ | $-C_{12}H_{25}$ | O | Cl, Br, I |
| 424 | " | H— | $-CH_3$ | S | Cl, Br, I |
| 425 | (dicyclohexyl)$COOCH_2CH_3-N(C_2H_5)_2$ (DICYCLOMINE) | H— | $-C_6H_5$ | O | Cl, Br, I |
| 426 | " | H— | $-C(CH_3)_3$ | O | Cl, Br, I |
| 427 | " | H— | $-C_5H_{11}$ | O | Cl, Br, I |
| 428 | " | H— | $-C_{12}H_{25}$ | O | Cl, Br, I |
| 429 | " | $CH_3-$ | $-C_6H_5$ | O | Cl, Br, I |
| 430 | " | $CH_3-$ | $-C(CH_3)_3$ | O | Cl, Br, I |
| 431 | " | $CH_3-$ | $-C_5H_{11}$ | O | Cl, Br, I |
| 432 | " | $CH_3-$ | $-C_{12}H_{25}$ | O | Cl, Br, I |
| 433 | " | $CCl_3-$ | $-C_6H_5$ | O | Cl, Br, I |
| 434 | " | $CCl_3-$ | $-C(CH_3)_3$ | O | Cl, Br, I |
| 435 | " | $CCl_3-$ | $-C_5H_{11}$ | O | Cl, Br, I |
| 436 | " | $CCl_3-$ | $-C_{12}H_{25}$ | O | Cl, Br, I |
| 437 | " | $C_6H_5-$ | $-C_6H_5$ | O | Cl, Br, I |

TABLE II-continued $$R-CH-\overset{\oplus}{N}\diagup \quad Y^{\ominus} \qquad R-CH-N\diagup \quad Y^{\ominus}$$
$$\underset{O}{\overset{|}{X-C-R_1}} \qquad \qquad \underset{O}{\overset{|}{X-C-R_1}}$$

| Ex. | $\diagdown N$ or $\diagdown N$ | R | $R_1$ | X | Y |
|---|---|---|---|---|---|
| 438 | " | $C_6H_5-$ | $-C(CH_3)_3$ | O | Cl, Br, I |
| 439 | " | $C_6H_5-$ | $-C_5H_{11}$ | O | Cl, Br, I |
| 440 | " | $C_6H_5-$ | $-C_{12}H_{25}$ | O | Cl, Br, I |
| 441 | " | H— | $-CH_3$ | S | Cl, Br, I |
| 442 | " | H— | $-C_6H_5$ | O | Cl, Br, I |
| | (PIPERIDOLATE) [structure: $(C_6H_5)_2CH-C(=O)-O-$ piperidyl-$N-C_2H_5$] | | | | |
| 443 | " | H— | $-C(CH_3)_3$ | O | Cl, Br, I |
| 444 | " | H— | $-C_5H_{11}$ | O | Cl, Br, I |
| 445 | " | H— | $-C_{12}H_{25}$ | O | Cl, Br, I |
| 446 | " | $CH_3-$ | $-C_6H_5$ | O | Cl, Br, I |
| 447 | " | $CH_3-$ | $-C(CH_3)_3$ | O | Cl, Br, I |
| 448 | " | $CH_3-$ | $-C_5H_{11}$ | O | Cl, Br, I |
| 449 | " | $CH_3-$ | $-C_{12}H_{25}$ | O | Cl, Br, I |
| 450 | " | $CCl_3-$ | $-C_6H_5$ | O | Cl, Br, I |
| 451 | " | $CCl_3-$ | $-C(CH_3)_3$ | O | Cl, Br, I |
| 452 | " | $CCl_3-$ | $-C_5H_{11}$ | O | Cl, Br, I |
| 453 | " | $CCl_3-$ | $-C_{12}H_{25}$ | O | Cl, Br, I |
| 454 | " | $C_6H_5-$ | $-C_6H_5$ | O | Cl, Br, I |
| 455 | " | $C_6H_5$ | $-C(CH_3)_3$ | O | Cl, Br, I |
| 456 | " | $C_6H_5-$ | $-C_5H_{11}$ | O | Cl, Br, I |
| 457 | " | $C_6H_5-$ | $-C_{12}H_{25}$ | O | Cl, Br, I |
| 458 | " | H— | $-CH_3$ | S | Cl, Br, I |
| 459 | " | H— | $-C_6H_5$ | O | Cl, Br, I |
| | (THIPHENAMIL) [structure: $(C_6H_5)_2CH-C(=O)-S-CH_2CH_2-N(C_2H_5)_2$] | | | | |
| 460 | " | H— | $-C(CH_3)_3$ | O | Cl, Br, I |
| 461 | " | H— | $-C_5H_{11}$ | O | Cl, Br, I |
| 462 | " | H— | $-C_{12}H_{25}$ | O | Cl, Br, I |
| 463 | " | $CH_3-$ | $-C_6H_5$ | O | Cl, Br, I |
| 464 | " | $CH_3-$ | $-C(CH_3)_3$ | O | Cl, Br, I |
| 465 | " | $CH_3-$ | $-C_5H_{11}$ | O | Cl, Br, I |
| 466 | " | $CH_3-$ | $-C_{12}H_{25}$ | O | Cl, Br, I |
| 467 | " | $CCl_3-$ | $-C_6H_5$ | O | Cl, Br, I |

TABLE II-continued $$R-CH-\overset{\oplus}{N}\diagdown \quad Y^{\ominus} \qquad R-CH-N\diagdown \quad Y^{\ominus}$$
$$\underset{O}{X-C-R_1} \qquad \underset{O}{X-C-R_1}$$

| Ex. | $\diagdown N$ or $\diagdown N$ | R | $R_1$ | X | Y |
|---|---|---|---|---|---|
| 468 | " | CCl₃— | —C(CH₃)₃ | O | Cl, Br, I |
| 469 | " | CCl₃— | —C₅H₁₁ | O | Cl, Br, I |
| 470 | " | CCl₃— | —C₁₂H₂₅ | O | Cl, Br, I |
| 471 | " | C₆H₅— | —C₆H₅ | O | Cl, Br, I |
| 472 | " | C₆H₅— | —C(CH₃)₃ | O | Cl, Br, I |
| 473 | " | C₆H₅— | —C₅H₁₁ | O | Cl, Br, I |
| 474 | " | C₆H₅— | —C₁₂H₂₅ | O | Cl, Br, I |
| 475 | " | H— | —CH₃ | S | Cl, Br, I |
| 476 | " | H— | —C₆H₅ | O | Cl, Br, I |

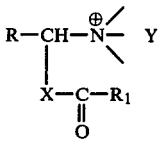
(PIPOXOLAN)

| Ex. | | R | $R_1$ | X | Y |
|---|---|---|---|---|---|
| 477 | " | H— | —C(CH₃)₃ | O | Cl, Br, I |
| 478 | " | H— | —C₅H₁₁ | O | Cl, Br, I |
| 479 | " | H— | —C₁₂H₂₅ | O | Cl, Br, I |
| 480 | " | CH₃— | —C₆H₅ | O | Cl, Br, I |
| 481 | " | CH₃— | —C(CH₃)₃ | O | Cl, Br, I |
| 482 | " | CH₃— | —C₅H₁₁ | O | Cl, Br, I |
| 483 | " | CH₃— | —C₁₂H₂₅ | O | Cl, Br, I |
| 484 | " | CCl₃— | —C₆H₅ | O | Cl, Br, I |
| 485 | " | CCl₃— | —C(CH₃)₃ | O | Cl, Br, I |
| 486 | " | CCl₃— | —C₅H₁₁ | O | Cl, Br, I |
| 487 | " | CCl₃— | —C₁₂H₂₅ | O | Cl, Br, I |
| 488 | " | C₆H₅— | —C₆H₅ | O | Cl, Br, I |
| 489 | " | C₆H₅— | —C(CH₃)₃ | O | Cl, Br, I |
| 490 | " | C₆H₅— | —C₅H₁₁ | O | Cl, Br, I |
| 491 | " | C₆H₅— | —C₁₂H₂₅ | O | Cl, Br, I |
| 492 | " | H— | —CH₃ | S | Cl, Br, I |
| 493 | 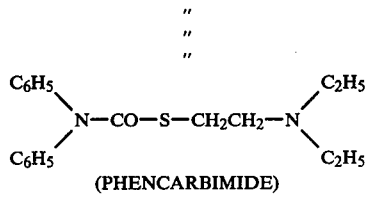 | H— | —C₆H₅ | O | Cl, Br, I |

(PHENCARBIMIDE)

| Ex. | | R | $R_1$ | X | Y |
|---|---|---|---|---|---|
| 494 | " | H— | —C(CH₃)₃ | O | Cl, Br, I |
| 495 | " | H— | —C₅H₁₁ | O | Cl, Br, I |
| 496 | " | H— | —C₁₂H₂₅ | O | Cl, Br, I |
| 497 | " | CH₃— | —C₆H₅ | O | Cl, Br, I |

TABLE II-continued

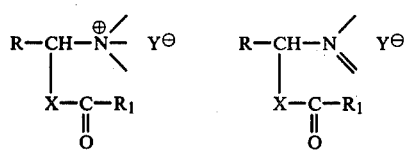

| Ex. | ⟩N or ⟩N | R | R₁ | X | Y |
|---|---|---|---|---|---|
| 498 | " | CH₃— | —C(CH₃)₃ | O | Cl, Br, I |
| 499 | " | CH₃— | —C₅H₁₁ | O | Cl, Br, I |
| 500 | " | CH₃— | —C₁₂H₂₅ | O | Cl, Br, I |
| 501 | " | CCl₃— | —C₆H₅ | O | Cl, Br, I |
| 502 | " | CCl₃— | —C(CH₃)₃ | O | Cl, Br, I |
| 503 | " | CCl₃— | —C₅H₁₁ | O | Cl, Br, I |
| 504 | " | CCl₃— | —C₁₂H₂₅ | O | Cl, Br, I |
| 505 | " | C₆H₅— | —C₆H₅ | O | Cl, Br, I |
| 506 | " | C₆H₅— | —C(CH₃)₃ | O | Cl, Br, I |
| 507 | " | C₆H₅— | —C₅H₁₁ | O | Cl, Br, I |
| 508 | " | C₆H₅— | —C₁₂H₂₅ | O | Cl, Br, I |
| 509 | " | H— | —CH₃ | S | Cl, Br, I |
| 510 | (TREMORINE: pyrrolidine-CH₂-C≡C-CH₂-pyrrolidine) | H— | —C₆H₅ | O | Cl, Br, I |
| 511 | " | H— | —C(CH₃)₃ | O | Cl, Br, I |
| 512 | " | H— | —C₅H₁₁ | O | Cl, Br, I |
| 513 | " | H— | —C₁₂H₂₅ | O | Cl, Br, I |
| 514 | " | CH₃— | —C₆H₅ | O | Cl, Br, I |
| 515 | " | CH₃— | —C(CH₃)₃ | O | Cl, Br, I |
| 516 | " | CH₃— | —C₅H₁₁ | O | Cl, Br, I |
| 517 | " | CH₃— | —C₁₂H₂₅ | O | Cl, Br, I |
| 518 | " | CCl₃— | —C₆H₅ | O | Cl, Br, I |
| 519 | " | CCl₃— | —C(CH₃)₃ | O | Cl, Br, I |
| 520 | " | CCl₃— | —C₅H₁₁ | O | Cl, Br, I |
| 521 | " | CCl₃— | —C₁₂H₂₅ | O | Cl, Br, I |
| 522 | " | C₆H₅— | —C₆H₅ | O | Cl, Br, I |
| 523 | " | C₆H₅— | —C(CH₃)₃ | O | Cl, Br, I |
| 524 | " | C₆H₅— | —C₅H₁₁ | O | Cl, Br, I |
| 525 | " | C₆H₅— | —C₁₂H₂₅ | O | Cl, Br, I |
| 526 | " | H— | —CH₃ | S | Cl, Br, I |
| 527 | 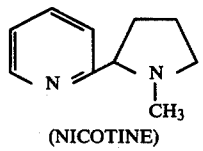 (NICOTINE) | H— | —C₆H₅ | O | Cl, Br, I |

TABLE II-continued $$R-CH-\overset{\oplus}{N}\diagup \quad Y^{\ominus} \qquad R-CH-N\diagup \quad Y^{\ominus}$$
$$\underset{\underset{O}{\overset{\|}{X-C-R_1}}}{\qquad} \qquad \underset{\underset{O}{\overset{\|}{X-C-R_1}}}{\qquad}$$

| Ex. | $\diagdown$N or $\diagdown$N | R | $R_1$ | X | Y |
|---|---|---|---|---|---|
| 528 | " | H— | —C(CH₃)₃ | O | Cl, Br, I |
| 529 | " | H— | —C₅H₁₁ | O | Cl, Br, I |
| 530 | " | H— | —C₁₂H₂₅ | O | Cl, Br, I |
| 531 | " | CH₃— | —C₆H₅ | O | Cl, Br, I |
| 532 | " | CH₃— | —C(CH₃)₃ | O | Cl, Br, I |
| 533 | " | CH₃— | —C₅H₁₁ | O | Cl, Br, I |
| 534 | " | CH₃— | —C₁₂H₂₅ | O | Cl, Br, I |
| 535 | " | CCl₃— | —C₆H₅ | O | Cl, Br, I |
| 536 | " | CCl₃— | —C(CH₃)₃ | O | Cl, Br, I |
| 537 | " | CCl₃— | —C₅H₁₁ | O | Cl, Br, I |
| 538 | " | CCl₃— | —C₁₂H₂₅ | O | Cl, Br, I |
| 539 | " | C₆H₅— | —C₆H₅ | O | Cl, Br, I |
| 540 | " | C₆H₅— | —C(CH₃)₃ | O | Cl, Br, I |
| 541 | " | C₆H₅— | —C₅H₁₁ | O | Cl, Br, I |
| 542 | " | C₆H₅— | —C₁₂H₂₅ | O | Cl, Br, I |
| 543 | " | H— | —CH₃ | S | Cl, Br, I |
| 544 | C₆H₅—CH—N⟩—COOC₃H₇ with CH₃ (PROPOXATE) | H— | —C₆H₅ | O | Cl, Br, I |
| 545 | " | H— | —C(CH₃)₃ | O | Cl, Br, I |
| 546 | " | H— | —C₅H₁₁ | O | Cl, Br, I |
| 547 | " | H— | —C₁₂H₂₅ | O | Cl, Br, I |
| 548 | " | CH₃— | —C₆H₅ | O | Cl, Br, I |
| 549 | " | CH₃— | —C(CH₃)₃ | O | Cl, Br, I |
| 550 | " | CH₃— | —C₅H₁₁ | O | Cl, Br, I |
| 551 | " | CH₃— | —C₁₂H₂₅ | O | Cl, Br, I |
| 552 | " | CCl₃— | —C₆H₅ | O | Cl,.Br, I |
| 553 | " | CCl₃— | —C(CH₃)₃ | O | Cl, Br, I |
| 554 | " | CCl₃— | —C₅H₁₁ | O | Cl, Br, I |
| 555 | " | CCl₃— | —C₁₂H₂₅ | O | Cl, Br, I |
| 556 | " | C₆H₅— | —C₆H₅ | O | Cl, Br, I |
| 557 | " | C₆H₅— | —C(CH₃)₃ | O | Cl, Br, I |
| 558 | " | C₆H₅— | —C₅H₁₁ | O | Cl, Br, I |
| 559 | " | C₆H₅— | —C₁₂H₂₅ | O | Cl, Br, I |
| 560 | " | H— | —CH₃ | S | Cl, Br, I |

TABLE II-continued $$R-CH-\overset{\oplus}{N}\diagup \quad Y^\ominus \qquad R-CH-N\diagup \quad Y^\ominus$$
$$\underset{\underset{O}{\parallel}}{X-C-R_1} \qquad \underset{\underset{O}{\parallel}}{X-C-R_1}$$

| Ex. | $\diagdown$N— or $\diagdown$N$\diagup$ | R | $R_1$ | X | Y |
|---|---|---|---|---|---|
| 561 | CH₃OOC-CH—CH—CH₂<br>C₆H₅COO—CH  N—CH₃<br>CH₂—CH—CH₂<br>(COCAINE) | H— | —C₆H₅ | O | Cl, Br, I |
| 562 | " | H— | —C(CH₃)₃ | O | Cl, Br, I |
| 563 | " | H— | —C₅H₁₁ | O | Cl, Br, I |
| 564 | " | H— | —C₁₂H₂₅ | O | Cl, Br, I |
| 565 | " | CH₃— | —C₆H₅ | O | Cl, Br, I |
| 566 | " | CH₃— | —C(CH₃)₃ | O | Cl, Br, I |
| 567 | " | CH₃— | —C₅H₁₁ | O | Cl, Br, I |
| 568 | " | CH₃— | —C₁₂H₂₅ | O | Cl, Br, I |
| 569 | " | CCl₃— | —C₆H₅ | O | Cl, Br, I |
| 570 | " | CCl₃— | —C(CH₃)₃ | O | Cl, Br, I |
| 571 | " | CCl₃— | —C₅H₁₁ | O | Cl, Br, I |
| 572 | " | CCl₃— | —C₁₂H₂₅ | O | Cl, Br, I |
| 573 | " | C₆H₅— | —C₆H₅ | O | Cl, Br, I |
| 574 | " | C₆H₅— | —C(CH₃)₃ | O | Cl, Br, I |
| 575 | " | C₆H₅— | —C₅H₁₁ | O | Cl, Br, I |
| 576 | " | C₆H₅— | —C₁₂H₂₅ | O | Cl, Br, I |
| 577 | " | H— | —CH₃ | S | Cl, Br, I |
| 578 | C₆H₅COO—CH₂CH₂CH₂—N(CH₃-piperidine)<br>(PIPEROCAINE) | H— | —C₆H₅ | O | Cl, Br, I |
| 579 | " | H— | —C(CH₃)₃ | O | Cl, Br, I |
| 580 | " | H— | —C₅H₁₁ | O | Cl, Br, I |
| 581 | " | H— | —C₁₂H₂₅ | O | Cl, Br, I |
| 582 | " | CH₃— | —C₆H₅ | O | Cl, Br, I |
| 583 | " | CH₃— | —C(CH₃)₃ | O | Cl, Br, I |
| 584 | " | CH₃— | —C₅H₁₁ | O | Cl, Br, I |
| 585 | " | CH₃— | —C₁₂H₂₅ | O | Cl, Br, I |
| 586 | " | CCl₃— | —C₆H₅ | O | Cl, Br, I |
| 587 | " | CCl₃— | —C(CH₃)₃ | O | Cl, Br, I |
| 588 | " | CCl₃— | —C₅H₁₁ | O | Cl, Br, I |
| 589 | " | CCl₃— | —C₁₂H₂₅ | O | Cl, Br, I |
| 590 | " | C₆H₅— | —C₆H₅ | O | Cl, Br, I |

TABLE II-continued $$R-CH-\overset{\oplus}{\underset{X-C-R_1}{N}}\diagdown\quad Y^{\ominus}\qquad R-CH-\underset{X-C-R_1}{N}\diagup\quad Y^{\ominus}$$
$$\underset{O}{\|}\qquad\qquad\qquad\underset{O}{\|}$$

| Ex. | $\diagdown N\diagdown$ or $\diagdown N\diagdown$ | R | $R_1$ | X | Y |
|---|---|---|---|---|---|
| 591 | " | $C_6H_5-$ | $-C(CH_3)_3$ | O | Cl, Br, I |
| 592 | " | $C_6H_5-$ | $-C_5H_{11}$ | O | Cl, Br, I |
| 593 | " | $C_6H_5-$ | $-C_{12}H_{25}$ | O | Cl, Br, I |
| 594 | " | H— | $-CH_3$ | S | Cl, Br, I |
| 595 | (DIBUCAINE) CO—NH—CH₂CH₂—N(C₂H₅)₂ on quinoline with O—C₄H₉ | H— | $-C_6H_5$ | O | Cl, Br, I |
| 596 | " | H— | $-C(CH_3)_3$ | O | Cl, Br, I |
| 597 | " | H— | $-C_5H_{11}$ | O | Cl, Br, I |
| 598 | " | H— | $-C_{12}H_{25}$ | O | Cl, Br, I |
| 599 | " | $CH_3-$ | $-C_6H_5$ | O | Cl, Br, I |
| 600 | " | $CH_3-$ | $-C(CH_3)_3$ | O | Cl, Br, I |
| 601 | " | $CH_3-$ | $-C_5H_{11}$ | O | Cl, Br, I |
| 602 | " | $CH_3-$ | $-C_{12}H_{25}$ | O | Cl, Br, I |
| 603 | " | $CCl_3-$ | $-C_6H_5$ | O | Cl, Br, I |
| 604 | " | $CCl_3-$ | $-C(CH_3)_3$ | O | Cl, Br, I |
| 605 | " | $CCl_3-$ | $-C_5H_{11}$ | O | Cl, Br, I |
| 606 | " | $CCl_3-$ | $-C_{12}H_{25}$ | O | Cl, Br, I |
| 607 | " | $C_6H_5-$ | $-C_6H_5$ | O | Cl, Br, I |
| 608 | " | $C_6H_5-$ | $-C(CH_3)_3$ | O | Cl, Br, I |
| 609 | " | $C_6H_5-$ | $-C_5H_{11}$ | O | Cl, Br, I |
| 610 | " | $C_6H_5-$ | $-C_{12}H_{25}$ | O | Cl, Br, I |
| 611 | " | H— | $-CH_3$ | S | Cl, Br, I |
| 612 | " | H— | $-C_6H_5$ | O | Cl, Br, I |
| 613 | (MEPIVACAINE) 2,6-dimethylphenyl-NH—CO-(N-methylpiperidin-2-yl) | H— | $-C(CH_3)_3$ | O | Cl, Br, I |
| 614 | " | H— | $-C_5H_{11}$ | O | Cl, Br, I |
| 615 | " | H— | $-C_{12}H_{25}$ | O | Cl, Br, I |
| 616 | " | $CH_3-$ | $-C_6H_5$ | O | Cl, Br, I |

TABLE II-continued $$R-CH-\overset{\oplus}{\underset{|}{N}}\diagdown \quad Y^{\ominus} \qquad R-CH-N\diagdown \quad Y^{\ominus}$$
$$\underset{X-C-R_1}{|} \qquad \underset{X-C-R_1}{|}$$
$$\underset{O}{\parallel} \qquad \underset{O}{\parallel}$$

| Ex. | $\diagdown N$ or $\diagup N$ | R | $R_1$ | X | Y |
|---|---|---|---|---|---|
| 617 | " | $CH_3-$ | $-C(CH_3)_3$ | O | Cl, Br, I |
| 618 | " | $CH_3-$ | $-C_5H_{11}$ | O | Cl, Br, I |
| 619 | " | $CH_3-$ | $-C_{12}H_{25}$ | O | Cl, Br, I |
| 620 | " | $CCl_3-$ | $-C_6H_5$ | O | Cl, Br, I |
| 621 | " | $CCl_3-$ | $-C(CH_3)_3$ | O | Cl, Br, I |
| 622 | " | $CCl_3-$ | $-C_5H_{11}$ | O | Cl, Br, I |
| 623 | " | $CCl_3-$ | $-C_{12}H_{25}$ | O | Cl, Br, I |
| 624 | " | $C_6H_5-$ | $-C_6H_5$ | O | Cl, Br, I |
| 625 | " | $C_6H_5-$ | $-C(CH_3)_3$ | O | Cl, Br, I |
| 626 | " | $C_6H_5-$ | $-C_5H_{11}$ | O | Cl, Br, I |
| 627 | " | $C_6H_5-$ | $-C_{12}H_{25}$ | O | Cl, Br, I |
| 628 | " | $H-$ | $-CH_3$ | S | Cl, Br, I |
| 629 | $C_6H_5-NH-COCH_2-N\diagup\diagdown$ (PYRROCAINE) | $H-$ | $-C_6H_5$ | O | Cl, Br, I |
| 630 | " | $H-$ | $-C(CH_3)_3$ | O | Cl, Br, I |
| 631 | " | $H-$ | $-C_5H_{11}$ | O | Cl, Br, I |
| 632 | " | $H-$ | $-C_{12}H_{25}$ | O | Cl, Br, I |
| 633 | " | $CH_3-$ | $-C_6H_5$ | O | Cl, Br, I |
| 634 | " | $CH_3-$ | $-C(CH_3)_3$ | O | Cl, Br, I |
| 635 | " | $CH_3$ | $-C_5H_{11}$ | O | Cl, Br, I |
| 636 | " | $CH_3-$ | $-C_{12}H_{25}$ | O | Cl, Br, I |
| 637 | " | $CCl_3-$ | $-C_6H_5$ | O | Cl, Br, I |
| 638 | " | $CCl_3-$ | $-C(CH_3)_3$ | O | Cl, Br, I |
| 639 | " | $CCl_3-$ | $-C_5H_{11}$ | O | Cl, Br, I |
| 640 | " | $CCl_3-$ | $-C_{12}H_{25}$ | O | Cl, Br, I |
| 641 | " | $C_6H_5-$ | $-C_6H_5$ | O | Cl, Br, I |
| 642 | " | $C_6H_5-$ | $-C(CH_3)_3$ | O | Cl, Br, I |
| 643 | " | $C_6H_5-$ | $-C_5H_{11}$ | O | Cl, Br, I |
| 644 | " | $C_6H_5-$ | $-C_{12}H_{25}$ | O | Cl, Br, I |
| 645 | " | $H-$ | $-CH_3$ | S | Cl, Br, I |
| 646 | $C_4H_9O-C_6H_4-O-CH_2CH_2CH_2-N\diagup\diagdown O$ (PRAMOXINE) | H | $-C_6H_5$ | O | Cl, Br, I |

TABLE II-continued $$R-CH-\overset{\oplus}{N}\diagup \quad Y^{\ominus} \qquad R-CH-N\diagup \quad Y^{\ominus}$$
$$\underset{\underset{O}{\|}}{X-C-R_1} \qquad \underset{\underset{O}{\|}}{X-C-R_1}$$

| Ex. | $\diagdown$N or $=$N | R | $R_1$ | X | Y |
|---|---|---|---|---|---|
| 647 | " | H— | —C(CH₃)₃ | O | Cl, Br, I |
| 648 | " | H— | —C₅H₁₁ | O | Cl, Br, I |
| 649 | " | H— | —C₁₂H₂₅ | O | Cl, Br, I |
| 650 | " | CH₃— | —C₆H₅ | O | Cl, Br, I |
| 651 | " | CH₃— | —C(CH₃)₃ | O | Cl, Br, I |
| 652 | " | CH₃— | —C₅H₁₁ | O | Cl, Br, I |
| 653 | " | CH₃— | —C₁₂H₂₅ | O | Cl, Br, I |
| 654 | " | CCl₃— | —C₆H₅ | O | Cl, Br, I |
| 655 | " | CCl₃— | —C(CH₃)₃ | O | Cl, Br, I |
| 656 | " | CCl₃— | —C₅H₁₁ | O | Cl, Br, I |
| 657 | " | CCl₃— | —C₁₂H₂₅ | O | Cl, Br, I |
| 658 | " | C₆H₅— | —C₆H₅ | O | Cl, Br, I |
| 659 | " | C₆H₅— | —C(CH₃)₃ | O | Cl, Br, I |
| 660 | " | C₆H₅— | —C₅H₁₁ | O | Cl, Br, I |
| 661 | " | C₆H₅— | —C₁₂H₂₅ | O | Cl, Br, I |
| 662 | " | H— | —CH₃ | S | Cl, Br, I |
| 663 | C₆H₅CH₂CH₂—N⟨piperidine⟩N(COC₂H₅)(C₆H₅) (FENTANYL) | H— | —C₆H₅ | O | Cl, Br, I |
| 664 | " | H— | —C(CH₃)₃ | O | Cl, Br, I |
| 665 | " | H— | —C₅H₁₁ | O | Cl, Br, I |
| 666 | " | H— | —C₁₂H₂₅ | O | Cl, Br, I |
| 667 | " | CH₃— | —C₆H₅ | O | Cl, Br, I |
| 668 | " | CH₃— | —C(CH₃)₃ | O | Cl, Br, I |
| 669 | " | CH₃— | —C₅H₁₁ | O | Cl, Br, I |
| 670 | " | CH₃— | —C₁₂H₂₅ | O | Cl, Br, I |
| 671 | " | CCl₃— | —C₆H₅ | O | Cl, Br, I |
| 672 | " | CCl₃— | —C(CH₃)₃ | O | Cl, Br, I |
| 673 | " | CCl₃— | —C₅H₁₁ | O | Cl, Br, I |
| 674 | " | CCl₃— | —C₁₂H₂₅ | O | Cl, Br, I |
| 675 | " | C₆H₅— | —C₆H₅ | O | Cl, Br, I |
| 676 | " | C₆H₅— | —C(CH₃)₃ | O | Cl, Br, I |
| 677 | " | C₆H₅— | —C₅H₁₁ | O | Cl, Br, I |
| 678 | " | C₆H₅— | —C₁₂H₂₅ | O | Cl, Br, I |
| 679 | " | H— | —CH₃ | S | Cl, Br, I |

TABLE II-continued

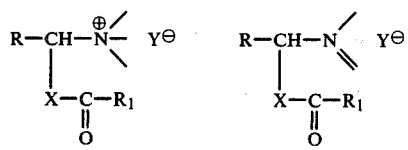

| Ex. | ⟩N or ⟩N= | R | R₁ | X | Y |
|---|---|---|---|---|---|
| 680 | [benzydamine structure with O-CH₂CH₂CH₂-N(CH₃)₂ group on bicyclic pyrazole bearing CH₂-C₆H₅] (BENZYDAMINE) | H— | —C₆H₅ | O | Cl, Br, I |
| 681 | " | H— | —C(CH₃)₃ | O | Cl, Br, I |
| 682 | " | H— | —C₅H₁₁ | O | Cl, Br, I |
| 683 | " | H— | —C₁₂H₂₅ | O | Cl, Br, I |
| 684 | " | CH₃— | —C₆H₅ | O | Cl, Br, I |
| 685 | " | CH₃— | —C(CH₃)₃ | O | Cl, Br, I |
| 686 | " | CH₃— | —C₅H₁₁ | O | Cl, Br, I |
| 687 | " | CH₃— | —C₁₂H₂₅ | O | Cl, Br, I |
| 688 | " | CCl₃— | —C₆H₅ | O | Cl, Br, I |
| 689 | " | CCl₃— | —C(CH₃)₃ | O | Cl, Br, I |
| 690 | " | CCl₃— | —C₅H₁₁ | O | Cl, Br, I |
| 691 | " | CCl₃— | —C₁₂H₂₅ | O | Cl, Br, I |
| 692 | " | C₆H₅— | —C₆H₅ | O | Cl, Br, I |
| 693 | " | C₆H₅— | —C(CH₃)₃ | O | Cl, Br, I |
| 694 | " | C₆H₅— | —C₅H₁₁ | O | Cl, Br, I |
| 695 | " | C₆H₅— | —C₁₂H₂₄ | O | Cl, Br, I |
| 696 | " | H— | —CH₃ | S | Cl, Br, I |
| 697 | C₂H₅—CO—C(C₆H₅)(C₆H₅)—C(CH₃)—CH₂—N(CH₃)(CH₃) (METHADONE) | H— | —C₆H₅ | O | Cl, Br, I |
| 698 | " | H— | —C(CH₃)₃ | O | Cl, Br, I |
| 699 | " | H— | —C₅H₁₁ | O | Cl, Br, I |
| 700 | " | H— | —C₁₂H₂₅ | O | Cl, Br, I |
| 701 | " | CH₃— | —C₆H₅ | O | Cl, Br, I |
| 702 | " | CH₃— | —C(CH₃)₃ | O | Cl, Br, I |
| 703 | " | CH₃— | —C₅H₁₁ | O | Cl, Br, I |
| 704 | " | CH₃— | —C₁₂H₂₅ | O | Cl, Br, I |
| 705 | " | CCl₃— | —C₆H₅ | O | Cl, Br, I |
| 706 | " | CCl₃— | —C(CH₃)₃ | O | Cl, Br, I |
| 707 | " | CCl₃— | —C₅H₁₁ | O | Cl, Br, I |
| 708 | " | CCl₃— | —C₁₂H₂₅ | O | Cl, Br, I |

TABLE II-continued $$R-CH-\overset{\oplus}{\underset{|}{N}}\diagdown \quad Y^{\ominus} \qquad R-CH-N\diagdown \quad Y^{\ominus}$$
$$\underset{|}{X-C-R_1} \qquad \underset{|}{X-C-R_1}$$
$$\underset{O}{\phantom{X}} \qquad \underset{O}{\phantom{X}}$$

| Ex. | $\diagdown N$ or $\diagdown N\diagup$ | R | $R_1$ | X | Y |
|---|---|---|---|---|---|
| 709 | " | $C_6H_5-$ | $-C_6H_5$ | O | Cl, Br, I |
| 710 | " | $C_6H_5-$ | $-C(CH_3)_3$ | O | Cl, Br, I |
| 711 | " | $C_6H_5-$ | $-C_5H_{11}$ | O | Cl, Br, I |
| 712 | " | $C_6H_5-$ | $-C_{12}H_{25}$ | O | Cl, Br, I |
| 713 | " | H— | $-CH_3$ | S | Cl, Br, I |
| 714 | (PROPOXYPHENE) 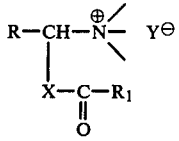 | H— | $-C_6H_5$ | O | Cl, Br, I |
| 715 | " | H— | $-C(CH_3)_3$ | O | Cl, Br, I |
| 716 | " | H— | $-C_5H_{11}$ | O | Cl, Br, I |
| 717 | " | H— | $-C_{12}H_{25}$ | O | Cl, Br, I |
| 718 | " | $CH_3-$ | $-C_6H_5$ | O | Cl, Br, I |
| 719 | " | $CH_3-$ | $-C(CH_3)_3$ | O | Cl, Br, I |
| 720 | " | $CH_3-$ | $-C_5H_{11}$ | O | Cl, Br, I |
| 721 | " | $CH_3-$ | $-C_{12}H_{25}$ | O | Cl, Br, I |
| 722 | " | $CCl_3-$ | $-C_6H_5$ | O | Cl, Br, I |
| 723 | " | $CCl_3-$ | $-C(CH_3)_3$ | O | Cl, Br, I |
| 724 | " | $CCl_3-$ | $-C_5H_{11}$ | O | Cl, Br, I |
| 725 | " | $CCl_3-$ | $-C_{12}H_{25}$ | O | Cl, Br, I |
| 726 | " | $C_6H_5-$ | $-C_6H_5$ | O | Cl, Br, I |
| 727 | " | $C_6H_5-$ | $-C(CH_3)_3$ | O | Cl, Br, I |
| 728 | " | $C_6H_5-$ | $-C_5H_{11}-$ | O | Cl, Br, I |
| 729 | " | $C_6H_5-$ | $-C_{12}H_{25}$ | O | Cl, Br, I |
| 730 | " | H— | $-CH_3$ | S | Cl, Br, I |
| 731 | (CHLORPROMAZINE) 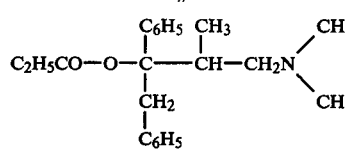 | H— | $-C_6H_5$ | O | Cl, Br, I |
| 732 | " | H— | $-C(CH_3)_3$ | O | Cl, Br, I |
| 733 | " | H— | $-C_5H_{11}$ | O | Cl, Br, I |
| 734 | " | H— | $-C_{12}H_{25}$ | O | Cl, Br, I |
| 735 | " | $CH_3-$ | $-C_6H_5$ | O | Cl, Br, I |
| 736 | " | $CH_3-$ | $-C(CH_3)_3$ | O | Cl, Br, I |

TABLE II-continued $$R-CH-\overset{+}{N}\diagdown\quad Y^{\ominus}\qquad R-CH-N\diagdown\quad Y^{\ominus}$$
$$\underset{\overset{\|}{O}}{X-C-R_1}\qquad\qquad \underset{\overset{\|}{O}}{X-C-R_1}$$

| Ex. | —N⟨ or ⟩N= | R | $R_1$ | X | Y |
|---|---|---|---|---|---|
| 737 | " | $CH_3$— | —$C_5H_{11}$ | O | Cl, Br, I |
| 738 | " | $CH_3$— | —$C_{12}H_{25}$ | O | Cl, Br, I |
| 739 | " | $CCl_3$— | —$C_6H_5$ | O | Cl, br, I |
| 740 | " | $CCl_3$— | —C(CH$_3$)$_3$ | O | Cl, Br, I |
| 741 | " | $CCl_3$— | —$C_5H_{11}$ | O | Cl, Br, I |
| 742 | " | $CCl_3$— | —$C_{12}H_{25}$ | O | Cl, Br, I |
| 743 | " | $C_6H_5$— | —$C_6H_5$ | O | Cl, Br, I |
| 744 | " | $C_6H_5$— | —C(CH$_3$)$_3$ | O | Cl, Br, I |
| 745 | " | $C_6H_5$— | —$C_5H_{11}$ | O | Cl, Br, I |
| 746 | " | $C_6H_5$— | —$C_{12}H_{25}$ | O | Cl, Br, I |
| 747 | " | H— | —$CH_3$ | S | Cl, Br, I |
| 748 | DIAZEPAM | H— | —$C_6H_5$ | O | Cl, Br, I |
| 749 | " | H— | —C(CH$_3$)$_3$ | O | Cl, Br, I |
| 750 | " | H— | —$C_5H_{11}$ | O | Cl, Br, I |
| 751 | " | H— | —$C_{12}H_{25}$ | O | Cl, Br, I |
| 752 | " | $CH_3$— | —$C_6H_5$ | O | Cl, Br, I |
| 753 | " | $CH_3$ | —C(CH$_3$)$_3$ | O | Cl, Br, I |
| 754 | " | $CH_3$ | —$C_5H_{11}$ | O | Cl, Br, I |
| 755 | " | $CH_3$— | —$C_{12}H_{25}$ | O | Cl, Br, I |
| 756 | " | $CCl_3$— | —$C_6H_5$ | O | Cl, Br, I |
| 757 | " | $CCl_3$— | —C(CH$_3$)$_3$ | O | Cl, Br, I |
| 758 | " | $CCl_3$— | —$C_5H_{11}$ | O | Cl, Br, I |
| 759 | " | $CCl_3$— | —$C_{12}H_{25}$ | O | Cl, Br, I |
| 760 | " | $C_6H_5$— | —$C_6H_5$ | O | Cl, Br, I |
| 761 | " | $C_6H_5$— | —C(CH$_3$)$_3$ | O | Cl, Br, I |
| 762 | " | $C_6H_5$— | —$C_5H_{11}$ | O | Cl, Br, I |
| 763 | " | $C_6H_5$— | —$C_{12}H_{25}$ | O | Cl, Br, I |
| 764 | " | H— | —$CH_3$ | S | Cl, Br, I |

TABLE II-continued

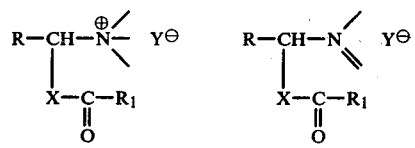

| Ex. | (structure) | R | R₁ | X | Y |
|---|---|---|---|---|---|
| 765 | CH₂CH₂—N(C₂H₅)₂ attached to flurazepam structure (FLURAZEPAM) | H— | —C₆H₅ | O | Cl, Br, I |
| 766 | " | H— | —C(CH₃)₃ | O | Cl, Br, I |
| 767 | " | H— | —C₅H₁₁ | O | Cl, Br, I |
| 768 | " | H— | —C₁₂H₂₅ | O | Cl, Br, I |
| 769 | " | CH₃— | —C₆H₅ | O | Cl, Br, I |
| 770 | " | CH₃— | —C(CH₃)₃ | O | Cl, Br, I |
| 771 | " | CH₃— | —C₅H₁₁ | O | Cl, Br, I |
| 772 | " | CH₃— | —C₁₂H₂₅ | O | Cl, Br, I |
| 773 | " | CCl₃— | —C₆H₅ | O | Cl, Br, I |
| 774 | " | CCl₃— | —C(CH₃)₃ | O | Cl, Br, I |
| 775 | " | CCl₃— | —C₅H₁₁ | O | Cl, Br, I |
| 776 | " | CCl₃— | —C₁₂H₂₅ | O | Cl, Br, I |
| 777 | " | C₆H₅— | —C₆H₅ | O | Cl, Br, I |
| 778 | " | C₆H₅— | —C(CH₃)₃ | O | Cl, Br, I |
| 779 | " | C₆H₅— | —C₅H₁₁ | O | Cl, Br, I |
| 780 | " | C₆H₅— | —C₁₂H₂₅ | O | Cl, Br, I |
| 781 | " | H— | —CH₃ | S | Cl, Br, I |
| 782 | cotinine structure (COTININE) | H— | —C₆H₅ | O | Cl, Br, I |
| 783 | " | H— | —C(CH₃)₃ | O | Cl, Br, I |
| 784 | " | H— | —C₅H₁₁ | O | Cl, Br, I |
| 785 | " | H— | —C₁₂H₂₅ | O | Cl, Br, I |
| 786 | " | CH₃— | —C₆H₅ | O | Cl, Br, I |
| 787 | " | CH₃— | —C(CH₃)₃ | O | Cl, Br, I |
| 788 | " | CH₃— | —C₅H₁₁ | O | Cl, Br, I |
| 789 | " | CH₃— | —C₁₂H₂₅ | O | Cl, Br, I |
| 790 | " | CCl₃— | —C₆H₅ | O | Cl, Br, I |

TABLE II-continued $$R-CH-\overset{\oplus}{\underset{|}{N}}\diagdown \quad Y^{\ominus} \qquad R-CH-N\diagdown \quad Y^{\ominus}$$
$$\underset{|}{X-\underset{\|}{C}-R_1} \qquad\qquad \underset{|}{X-\underset{\|}{C}-R_1}$$
$$\quad\; O \qquad\qquad\qquad\;\; O$$

| Ex. | $\diagdown\!\!-\!\!N\diagup$ or $\diagdown\!\!N\!\!=$ | R | $R_1$ | X | Y |
|---|---|---|---|---|---|
| 791 | " | $CCl_3-$ | $-C(CH_3)_3$ | O | Cl, Br, I |
| 792 | " | $CCl_3-$ | $-C_5H_{11}$ | O | Cl, Br, I |
| 793 | " | $CCl_3-$ | $-C_{12}H_{25}$ | O | Cl, Br, I |
| 794 | " | $C_6H_5-$ | $-C_6H_5$ | O | Cl, Br, I |
| 795 | " | $C_6H_5-$ | $-C(CH_3)_3$ | O | Cl, Br, I |
| 796 | " | $C_6H_5-$ | $-C_5H_{11}$ | O | Cl, Br, I |
| 797 | " | $C_6H_5-$ | $-C_{12}H_{25}$ | O | Cl, Br, I |
| 798 | " | $H-$ | $-CH_3$ | S | Cl, Br, I |
| 799 | (NIKETHAMIDE) | $H-$ | $-C_6H_5$ | O | Cl, Br, I |
| 800 | " | $H-$ | $-C(CH_3)_3$ | O | Cl, Br, I |
| 801 | " | $H-$ | $-C_5H_{11}$ | O | Cl, Br, I |
| 802 | " | $H-$ | $-C_{12}H_{25}$ | O | Cl, Br, I |
| 803 | " | $CH_3-$ | $-C_6H_5$ | O | Cl, Br, I |
| 804 | " | $CH_3-$ | $-C(CH_3)_3$ | O | Cl, Br, I |
| 805 | " | $CH_3-$ | $-C_5H_{11}$ | O | Cl, Br, I |
| 806 | " | $CH_3-$ | $-C_{12}H_{25}$ | O | Cl, Br, I |
| 807 | " | $CCl_3-$ | $-C_6H_5$ | O | Cl, Br, I |
| 808 | " | $CCl_3-$ | $-C(CH_3)_3$ | O | Cl, Br, I |
| 809 | " | $CCl_3-$ | $-C_5H_{11}$ | O | Cl, Br, I |
| 810 | " | $CCl_3-$ | $-C_{12}H_{25}$ | O | Cl, Br, I |
| 811 | " | $C_6H_5-$ | $-C_6H_5$ | O | Cl, Br, I |
| 812 | " | $C_6H_5-$ | $-C(CH_3)_3$ | O | Cl, Br, I |
| 813 | " | $C_6H_5-$ | $-C_5H_{11}$ | O | Cl, Br, I |
| 814 | " | $C_6H_5-$ | $-C_{12}H_{25}$ | O | Cl, Br, I |
| 815 | " | $H-$ | $-CH_3$ | S | Cl, Br, I |
| 816 | " | $H-$ | $-C_6H_5$ | O | Cl, Br, I |
| | (DOXAPRAM) | | | | |
| 817 | " | $H-$ | $-C(CH_3)_3$ | O | Cl, Br, I |
| 818 | " | $H-$ | $-C_5H_{11}$ | O | Cl, Br, I |
| 819 | " | $H-$ | $-C_{12}H_{25}$ | O | Cl, Br, I |
| 820 | " | $CH_3-$ | $-C_6H_5$ | O | Cl, Br, I |

TABLE II-continued $$\underset{\substack{| \\ X-C-R_1 \\ \| \\ O}}{R-CH-\overset{\oplus}{N}\diagup} Y^{\ominus} \qquad \underset{\substack{| \\ X-C-R_1 \\ \| \\ O}}{R-CH-N\diagdown} Y^{\ominus}$$

| Ex. | ≻N or ≻N | R | R$_1$ | X | Y |
|---|---|---|---|---|---|
| 821 | " | CH$_3$— | —C(CH$_3$)$_3$ | O | Cl, Br, I |
| 822 | " | CH$_3$— | —C$_5$H$_{11}$ | O | Cl, Br, I |
| 823 | " | CH$_3$— | —C$_{12}$H$_{25}$ | O | Cl, Br, I |
| 824 | " | CCl$_3$— | —C$_6$H$_5$ | O | Cl, Br, I |
| 825 | " | CCl$_3$— | —C(CH$_3$)$_3$ | O | Cl, Br, I |
| 826 | " | CCl$_3$— | —C$_5$H$_{11}$ | O | Cl, Br, I |
| 827 | " | CCl$_3$— | —C$_{12}$H$_{25}$ | O | Cl, Br, I |
| 828 | " | C$_6$H$_5$— | —C$_6$H$_5$ | O | Cl, Br, I |
| 829 | " | C$_6$H$_5$— | —C(CH$_3$)$_3$ | O | Cl, Br, I |
| 830 | " | C$_6$H$_5$— | —C$_5$H$_{11}$ | O | Cl, Br, I |
| 831 | " | C$_6$H$_5$— | —C$_{12}$H$_{25}$ | O | Cl, Br, I |
| 832 | " | H— | —CH$_3$ | S | Cl, Br, I |
| 833 | " | H— | —C$_6$H$_5$ | O | Cl, Br, I |
| | (STRYCHNINE) | | | | |
| 834 | " | H— | —C(CH$_3$)$_3$ | O | Cl, Br, I |
| 835 | " | H— | —C$_5$H$_{11}$ | O | Cl, Br, I |
| 836 | " | H— | —C$_{12}$H$_{25}$ | O | Cl, Br, I |
| 837 | " | CH$_3$— | —C$_6$H$_5$ | O | Cl, Br, I |
| 838 | " | CH$_3$— | —C(CH$_3$)$_3$ | O | Cl, Br, I |
| 839 | " | CH$_3$— | —C$_5$H$_{11}$ | O | Cl, Br, I |
| 840 | " | CH$_3$— | —C$_{12}$H$_{25}$ | O | Cl, Br, I |
| 841 | " | CCl$_3$— | —C$_6$H$_5$ | O | Cl, Br, I |
| 842 | " | CCl$_3$— | —C(CH$_3$)$_3$ | O | Cl, Br, I |
| 843 | " | CCl$_3$— | —C$_5$H$_{11}$ | O | Cl, Br, I |
| 844 | " | CCl$_3$— | —C$_{12}$H$_{25}$ | O | Cl, Br, I |
| 845 | " | C$_6$H$_5$— | —C$_6$H$_5$ | O | Cl, Br, I |
| 846 | " | C$_6$H$_5$— | —C(CH$_3$)$_3$ | O | Cl, Br, I |
| 847 | " | C$_6$H$_5$— | —C$_5$H$_{11}$ | O | Cl, Br, I |
| 848 | " | C$_6$H$_5$— | —C$_{12}$H$_{25}$ | O | Cl, Br, I |
| 849 | " | H— | —CH$_3$ | S | Cl, Br, I |

TABLE II-continued

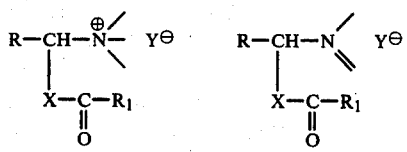

| Ex. | 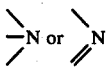 | R | R₁ | X | Y |
|---|---|---|---|---|---|
| 850 | (IMIPRAMINE structure with CH₂CH₂CH₂N(CH₃)₂) | H— | —C₆H₅ | O | Cl, Br, I |
| 851 | " | H— | —C(CH₃)₃ | O | Cl, Br, I |
| 852 | " | H— | —C₅H₁₁ | O | Cl, Br, I |
| 853 | " | H— | —C₁₂H₂₅ | O | Cl, Br, I |
| 854 | " | CH₃— | —C₆H₅ | O | Cl, Br, I |
| 855 | " | CH₃— | —C(CH₃)₃ | O | Cl, Br, I |
| 856 | " | CH₃— | —C₅H₁₁ | O | Cl, Br, I |
| 857 | " | CH₃— | —C₁₂H₂₅ | O | Cl, Br, I |
| 858 | " | CCl₃— | —C₆H₅ | O | Cl, Br, I |
| 859 | " | CCl₃— | —C(CH₃)₃ | O | Cl, Br, I |
| 860 | " | CCl₃— | —C₅H₁₁ | O | Cl, Br, I |
| 861 | " | CCl₃— | —C₁₂H₂₅ | O | Cl, Br, I |
| 862 | " | C₆H₅— | —C₆H₅ | O | Cl, Br, I |
| 863 | " | C₆H₅— | —C(CH₃)₃ | O | Cl, Br, I |
| 864 | " | C₆H₅— | —C₅H₁₁ | O | Cl, Br, I |
| 865 | " | C₆H₅— | —C₁₂H₂₅ | O | Cl, Br, I |
| 866 | " | H— | —CH₃ | S | Cl, Br, I |

As used in this application, the term "unsaturated amine" denotes N-heterocyclic unsaturated systems having 3–10 members in the ring, and substituted derivatives thereof where the unsaturation corresponds to the maximum number of noncumulative double bonds, provided that the nitrogen atom contains no hydrogen atom as a substituent. The following examples will sufficiently illustrate the scope of the above term:

1-Methyl-azirine 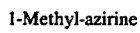

1-Methyl-pyrrole 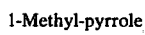

1-Methyl-imidazole 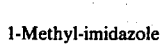

1-Methyl-pyrazole 

Pyridine

Pyrazine

Pyrimidine

Pyridazine

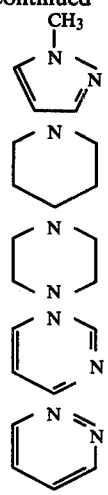

-continued

2-Methyl-isoindole 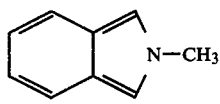

3-H-indole 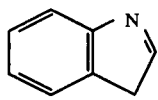

Quinoline 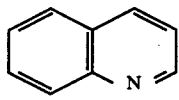

Isoquinoline 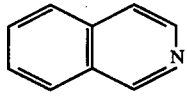

Phtalazine 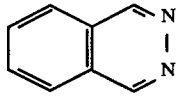

Quinoxiline 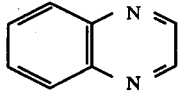

Quinazidine 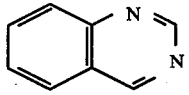

Phenazine 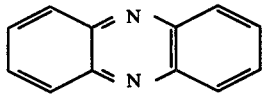

Isothiazole 

10-Methyl-phenothiazine 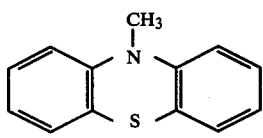

Isoxazole 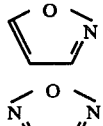

Furazan 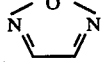

EXAMPLE 867

IN VITRO CLEAVAGE OF 1-METHYLIMIDAZOLE-3-BENZOYLOXYBENZYL CHLORIDE

1-Methylimidazole-3-benzoyloxybenzyl chloride was dissolved in water. A few drops of 1N NaOH solution was added to raise the pH to approximately 10-11. The smell of benzaldehyde could be detected, and after acidifying the solution, benzoic acid precipitates. The third component, 1-methylimidazole could be isolated by extraction with ether of the basified solution.

The "soft" quaternary salt thus cleaves back into the original components.

EXAMPLE 868

ENZYMATIC RELEASE OF LIDOCAINE FROM LIDOCAINE BENZOYLOXYMETHYL CHLORIDE

Lidocaine benzoyloxymethyl chloride (see Example 18) was dissolved in water. 0.5 ml of this solution (containing 50 mg of the compound) was incubated at 37° C. with 5 ml of human serum. Analysis of the solution after 30 minutes (be LC) indicated a complete cleavage of the quaternary salt, by 100% recovery of the lidocaine.

EXAMPLE 869

WR-30,090* - COMPARATIVE BIOAVAILABILITY STUDY

In some instance, the same Beagle dog was used for the comparative bioavailability study. The following compounds were administered and the appearance of WR-30,090 in blood was measured at various time intervals:

*a known antimalarial compound

WR-30,090 (1)

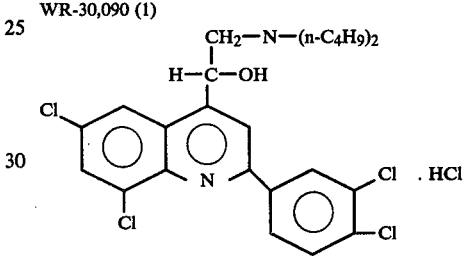

N,N-Dimethylglycinate of WR-30,090 (2)

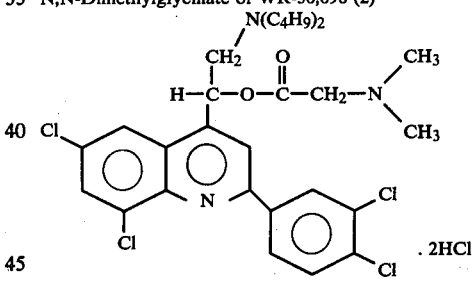

Labile Quaternary Ammonium Salt of the N,N-dimethylglycinate of WR-30,090 (3)

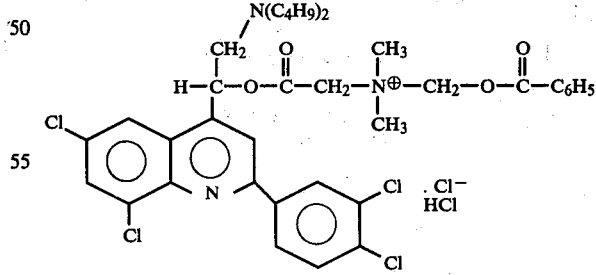

200

WR-30,090 (1) was administered as the hydrochloride salt, in a gelatin capsule containing 250 mg of the active compound. After administration of the capsule, a tube was inserted into the stomach of the dog and 200ml of water was given.

In the case of the N,N-dimethylglycinate derivative, per se (2) and the labile quaternary ammonium salt of the same (3), the material was given, on an equivalent TABLE II-continued

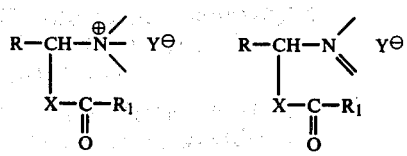

| Ex. | 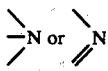 | R | $R_1$ | X | Y |
|---|---|---|---|---|---|
| 850 | (IMIPRAMINE) structure with dibenzazepine-CH₂CH₂CH₂N(CH₃)₂ | H— | —$C_6H_5$ | O | Cl, Br, I |
| 851 | " | H— | —C(CH₃)₃ | O | Cl, Br, I |
| 852 | " | H— | —$C_5H_{11}$ | O | Cl, Br, I |
| 853 | " | H— | —$C_{12}H_{25}$ | O | Cl, Br, I |
| 854 | " | $CH_3$— | —$C_6H_5$ | O | Cl, Br, I |
| 855 | " | $CH_3$— | —C(CH₃)₃ | O | Cl, Br, I |
| 856 | " | $CH_3$— | —$C_5H_{11}$ | O | Cl, Br, I |
| 857 | " | $CH_3$— | —$C_{12}H_{25}$ | O | Cl, Br, I |
| 858 | " | $CCl_3$— | —$C_6H_5$ | O | Cl, Br, I |
| 859 | " | $CCl_3$— | —C(CH₃)₃ | O | Cl, Br, I |
| 860 | " | $CCl_3$— | —$C_5H_{11}$ | O | Cl, Br, I |
| 861 | " | $CCl_3$— | —$C_{12}H_{25}$ | O | Cl, Br, I |
| 862 | " | $C_6H_5$— | —$C_6H_5$ | O | Cl, Br, I |
| 863 | " | $C_6H_5$— | —C(CH₃)₃ | O | Cl, Br, I |
| 864 | " | $C_6H_5$— | —$C_5H_{11}$ | O | Cl, Br, I |
| 865 | " | $C_6H_5$— | —$C_{12}H_{25}$ | O | Cl, Br, I |
| 866 | " | H— | —$CH_3$ | S | Cl, Br, I |

As used in this application, the term "unsaturated amine" denotes N-heterocyclic unsaturated systems having 3–10 members in the ring, and substituted derivatives thereof where the unsaturation corresponds to the maximum number of noncumulative double bonds, provided that the nitrogen atom contains no hydrogen atom as a substituent. The following examples will sufficiently illustrate the scope of the above term:

1-Methyl-azirine 

1-Methyl-pyrrole 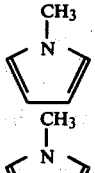

1-Methyl-imidazole 

1-Methyl-pyrazole

Pyridine

Pyrazine

Pyrimidine

Pyridazine

-continued

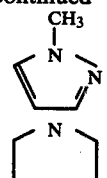

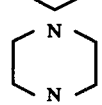

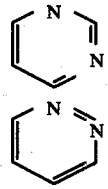

-continued

2-Methyl-isoindole 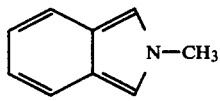

3-H-indole 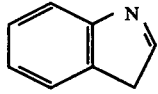

Quinoline 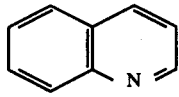

Isoquinoline 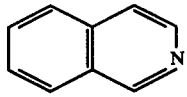

Phtalazine 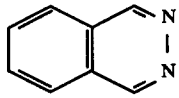

Quinoxiline 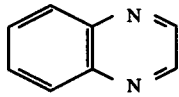

Quinazidine 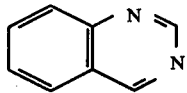

Phenazine 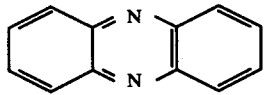

Isothiazole 

10-Methyl-phenothiazine 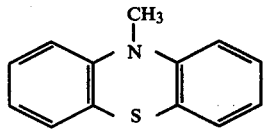

Isoxazole 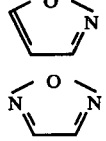

Furazan 

EXAMPLE 867

IN VITRO CLEAVAGE OF 1-METHYLIMIDAZOLE-3-BENZOYLOXYBEN-ZYL CHLORIDE

1-Methylimidazole-3-benzoyloxybenzyl chloride was dissolved in water. A few drops of 1N NaOH solution was added to raise the pH to approximately 10–11. The smell of benzaldehyde could be detected, and after acidifying the solution, benzoic acid precipitates. The third component, 1-methylimidazole could be isolated by extraction with ether of the basified solution.

The "soft" quaternary salt thus cleaves back into the original components.

EXAMPLE 868

ENZYMATIC RELEASE OF LIDOCAINE FROM LIDOCAINE BENZOYLOXYMETHYL CHLORIDE

Lidocaine benzoyloxymethyl chloride (see Example 18) was dissolved in water. 0.5 ml of this solution (containing 50 mg of the compound) was incubated at 37° C. with 5 ml of human serum. Analysis of the solution after 30 minutes (be LC) indicated a complete cleavage of the quaternary salt, by 100% recovery of the lidocaine.

EXAMPLE 869

WR-30,090* - COMPARATIVE BIOAVAILABILITY STUDY

In some instance, the same Beagle dog was used for the comparative bioavailability study. The following compounds were administered and the appearance of WR-30,090 in blood was measured at various time intervals:

*a known antimalarial compound

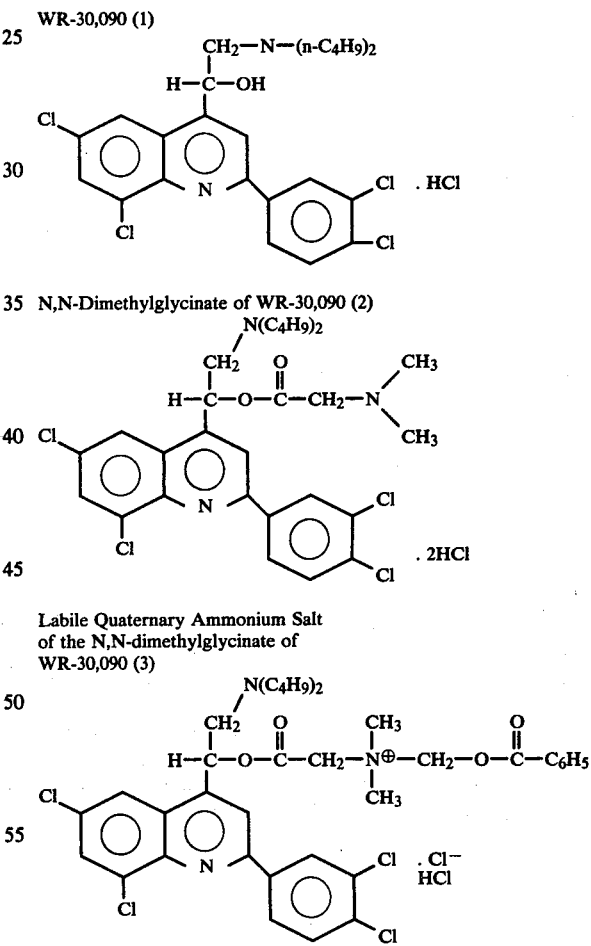

WR-30,090 (1) was administered as the hydrochloride salt, in a gelatin capsule containing 250 mg of the active compound. After administration of the capsule, a tube was inserted into the stomach of the dog and 200ml of water was given.

In the case of the N,N-dimethylglycinate derivative, per se (2) and the labile quaternary ammonium salt of the same (3), the material was given, on an equivalent molecular weight basis, in 50 ml of water (almost a complete solution), followed by 150 ml of water given through a tube. In each instance, the dog was fasted for 18 hours prior to each experiment and given food only after 24 hours following administration of each compound.

The attached FIG. 1 quite readily illustrates the blood levels of WR-30,090 measured at various times for each compound administered.

It can be seen that a dramatic increase in delivery of WR-30,090 via the labile quaternary salt form is achieved and that the derivative obviously "cleaves" back to the parent compound, WR-30,090, per se, following delivery.

ANALYTICAL PROCEDURE

In order to determine whether an increase in bioavailability of WR-30,090 could be achieved by a labile quaternary ammonium salt of the drug, some means of measuring the concentration of the drug in blood was necessary. Therefore, an analytical procedure was developed for the determination of WR-30,090 concentrations in whole blood. The procedure involves extraction of the drug from blood and the quantitative analysis of the extracted drug using the high-pressure liquid chromatographic method.

EXTRACTION PROCEDURE

Five milliliters of blood were used in these experiments. The blood was mixed with 2 drops of a 15% EDTA solution and shaken for 1 hour with 5 ml of ether in a glass centrifuge tube which was not siliconized. It was then centrifuged and frozen in dry ice - acetone after which, the ether layer was decanted into a glass conical-shaped centrifuge tube. The extraction procedure was repeated two (2) more times on this blood sample, and the combined ether fractions were evaporated using a rotary Evapo-Mix, test tube model, at room temperature. The centrifuge tubes were then completely dried overnight in a vacuum dessicator containing calcium chloride. The solid material was dissolved just prior to analysis with 100 μl of 20% chloroform — 80% heptane mixture. Usually 10 μl of this solution was injected on the column.

The recovery of WR-30,090 from spiked blood samples was determined using this extraction procedure. Table I shows some data for samples spiked with WR-30,090 shaken for 1 hour to allow equilibration and then extracted. The recovery is 80%, with a range of about 6% for samples of relatively high concentration. A larger variability was observed for spiked samples in the 50-100 ng/ml range. The cause of this variability is probably due to the column condition of the liquid chromatograph rather than the extraction procedure.

TABLE I

| Recovery Percentage of Spiked Blood Samples of WR-30,090 | | |
|---|---|---|
| Spiked Concentration | Percent Recovery[c] | |
| μg/ml of blood | Column 1[a] | Column 2[b] |
| 0.050 | 52 | 98 |
| 0.20 | 75 | 87 |
| 0.50 | 75 | 82 |
| 1.0 | 87 | 77 |
| 3.0 | 85 | 79 |

[a]Corasil Type II column using 20% dioxane:heptane as mobile phase.
[b]Corasil Type II column using 3-10% methanol in 20% dioxane-heptane mixture as mobile phase.
[c]Single runs on spiked blood samples.

HPLC ANALYSIS

A Varian Model 4000 high-pressure liquid chromatograph equipped with a UV absorption detector at 280 nm was used in the analysis. Corasil Type II packing material is the stationary phase. Several different mobile phases were tried in order to achieve a column which would be stable for as many as 400 injections. This has not proven possible; however, a system has been developed in which one column can be used for this number of injections, but at about every 40 injections the composition of the mobile phase needs to be changed slightly to retain good peak separation. A standard concentration of WR-30,090 free base in 20% chloroform - heptane is injected before and after each blood sample. The average area of the standard peaks is used to define the column sensitivity for that particular run. The mobile phase used with a fresh Corasil Type II column is 10% methanol by volume in the stock solvent (20% dioxane in heptane, v/v). The mobile phase is dried over anhydrous sodium sulfate and then degassed in order to achieve reproducible results. As the column is used, the separation of WR-30,090 free base from the blood components becomes worse and the amount of methanol must be decreased to give a good separation. The sensitivity of the analysis is also decreased. A column is used until the methanol concentration must be decreased to less than three percent to give a good separation.

EXAMPLE 870
PILOCARPINE - OPHTHALMIC MIOSIS STUDY

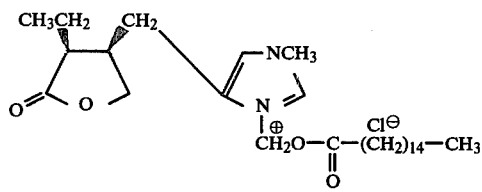

PILOCARPINE 3-N-HEXADECANOYLOXYMETHYL CHLORIDE

Figure 2:
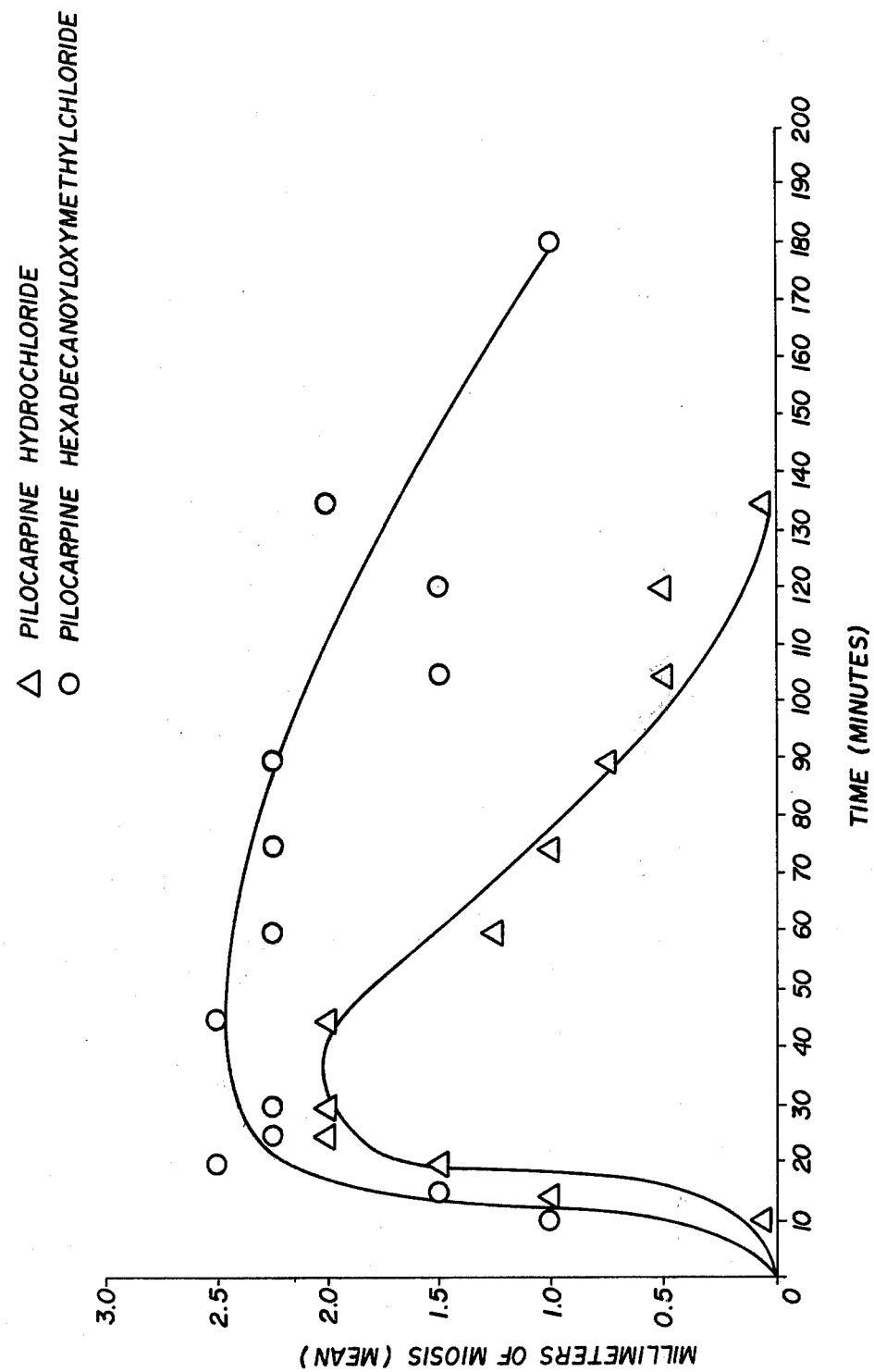

An equivalent of a 2% pilocarpine solution of the hydrochloride and the hexadecanoyloxymethyl chloride salt of pilocarpine were compared for miotic activity in the eyes of albino female rabbits. The results are represented graphically in FIG. 2 accompanying this declaration. It is quite obvious that the quaternary salt form (hexadecanoyloxymethyl chloride) that releases pilocarpine, but most importantly, at a more dramatic sustained rate when compound to pilocarpine, per se.

Similar results as obtained for the labile quaternary salts of Examples 867 and 868 will be obtained for the remaining compounds of the instant invention when tested under in vitro or in vivo conditions.

Based on the foregoing, it is quite obvious to any skilled artisan that any known therapeutically active tertiary aliphatic amine or unsaturated amine can be delivered via the compound generically described herein as chemical and/or enzymatic hydrolysis will automatically "cleave" such moiety to release its component parts, i.e., the tertiary aliphatic amine or unsaturated amine, an aldehyde and carboxylic acid moieties.

The dose and dosage form administered, whether a single dose or a daily dose, will, of course, vary because of the chosen route of administration, and the size of the recipient. The dosage administered is not subject to definite bounds, but it will usually be an effective amount, or the equivalent on a molar basis of the pharmacologically active form produced upon the metabolic release of the active drug to achieve its desired pharmacological and physiological effect. See, Physicians' Desk Reference, 29th Edition (1975).

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably, and intended to be, within the full range of equivalence of the following claims.

What I claim is:

1. A compound selected from the group consisting of ω-(diethyl-pivaloyloxymethyl-ammonium)-2,6-dimethyl-acetanilide chloride; N-ethylephedrine (α-acetyloxyethyl) chloride; 2-diethylaminopropiophenone heptanoyloxymethyl chloride; 6-dimethylamino-4,4-diphenyl-3-heptanone-N-heptanoyloxmethyl chloride; 6-dimethylamino-4,4-diphenyl-3-heptanone-N-acetyloxymethyl chloride; and 4-dimethylamino-3-methyl-1,2-diphenyl-2-butanol propionate N-hexanoyloxymethyl chloride.

2. The compound of claim 1:
ω-(Diethyl-pivaloyloxymethyl-ammonium)-2,6-dimethylacetanilidine chloride.

3. The compound of claim 1:
N-Ethylephedrine(α-acetyloxyethyl)chloride.

4. The compound of claim 1:
2-Diethylaminopropiophenone heptanoyloxymethyl chloride.

5. The compound of claim 1:
6Dimethylamino-4,4-diphenyl-3-heptanone-N-heptanoyloxymethyl chloride.

6. The compound of claim 1:
6-Dimethylamino-4,4-diphenyl-3-heptanone-N-acetyloxymethyl chloride.

7. The compound of claim 1:
4-Dimethylamino-3-methyl-1,2-diphenyl-2-butanol propionate N-hexanoyloxymethyl chloride.

* * * * *